US011413472B2

(12) United States Patent
Blivet et al.

(10) Patent No.: US 11,413,472 B2
(45) Date of Patent: Aug. 16, 2022

(54) OPTICAL GUIDE FOR DIFFUSING LIGHT RADIATION, MODULE AND DEVICE FOR TRANSCUTANEOUS IRRADIATION, IN PARTICULAR TRANSCRANIAL IRRADIATION

(71) Applicant: REGENLIFE, Montpellier (FR)

(72) Inventors: Guillaume Blivet, Montpellier (FR); Guillaume Moreau, Baillargues (FR); Etienne Cochard, Baillargues (FR)

(73) Assignee: REGENLIFE

( * ) Notice: Subject to any disclaimer, the term of this patent is extended or adjusted under 35 U.S.C. 154(b) by 0 days.

(21) Appl. No.: 16/970,062

(22) PCT Filed: Feb. 18, 2019

(86) PCT No.: PCT/EP2019/053984
§ 371 (c)(1),
(2) Date: Aug. 14, 2020

(87) PCT Pub. No.: WO2019/158758
PCT Pub. Date: Aug. 22, 2019

(65) Prior Publication Data
US 2021/0023390 A1 Jan. 28, 2021

(30) Foreign Application Priority Data
Feb. 16, 2018 (EP) .................................... 18305162

(51) Int. Cl.
*A61N 5/06* (2006.01)
*A61N 5/067* (2006.01)

(52) U.S. Cl.
CPC ......... *A61N 5/0622* (2013.01); *A61N 5/0618* (2013.01); *A61N 5/067* (2021.08);
(Continued)

(58) Field of Classification Search
CPC ................ A61N 5/0622; A61N 5/0618; A61N 2005/063; A61N 2005/0647;
(Continued)

(56) References Cited

U.S. PATENT DOCUMENTS 6,094,767 A * 8/2000 Iimura ............... A46B 15/0002
15/105
2003/0004556 A1 * 1/2003 McDaniel ................ A61K 8/67
607/88

(Continued)

FOREIGN PATENT DOCUMENTS

EP 2269692 A2 1/2011
EP 2269692 A2 * 5/2011 ............. A61N 5/067
WO 2008144157 A1 11/2008

OTHER PUBLICATIONS

Extended European Search Report including Written Opinion for Application No. EP18305162.2, dated Aug. 24, 2018, pp. 1-8.
(Continued)

*Primary Examiner* — Brian T Gedeon
*Assistant Examiner* — Joshua Andrew Schum-Houck
(74) *Attorney, Agent, or Firm* — Lerner, David, Littenberg, Krumholz & Mentlik, LLP

(57) ABSTRACT

The invention relates mainly to an optical guide for diffusing a light radiation through a surface, which is essentially characterized in that it includes a base (3,31) comprising or able to hold at least one diffusion rod (2, 2*a;* 35*a*, 35*b*, 35*c*) whose lower diffusion end (7, 7*a;* 38*a*, 38*b*, 38*c*) protrudes from said base (3) and is intended to be applied on or near said surface, and whose upper collecting end (6,6*a;* 37*a*, 37*b*, 37*c*) is intended to be located near and opposite a power supplied light source (36*a*, 36*b*, 36*c*), and in that the diffusion rod (2, 2*a;* 35*a*, 35*b*, 35*c*) comprises a material able to transmit light from its collecting end (6,6*a;* 37*a*, 37*b*, 37*c*) up to its diffusion end (7, 7*a;* 38*a*, 38*b*, 38*c*).

(Continued)

Figure 1:
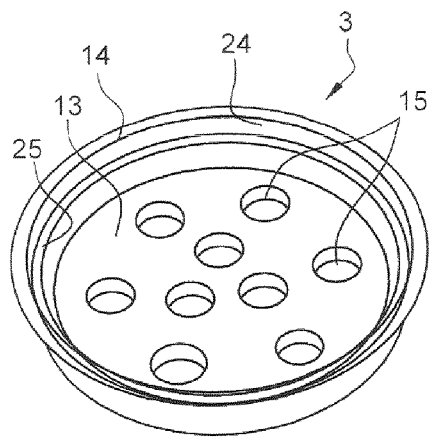

The invention also relates to an irradiation module and to an irradiation device adapted to the transcranial and/or transcutaneous irradiation by light radiation.

16 Claims, 19 Drawing Sheets

(52) U.S. Cl.
CPC .................. *A61N 2005/063* (2013.01); *A61N 2005/0647* (2013.01); *A61N 2005/0659* (2013.01)

(58) Field of Classification Search
CPC ...... A61N 2005/0659; A61N 2005/067; A61N 2005/0652
See application file for complete search history.

(56) References Cited

U.S. PATENT DOCUMENTS

| | | | |
|---|---|---|---|
| 2004/0116985 A1* | 6/2004 | Black | A61N 5/0603 607/89 |
| 2004/0193235 A1* | 9/2004 | Altshuler | A46B 15/0036 607/88 |
| 2004/0259053 A1* | 12/2004 | Bekov | A61C 17/20 433/119 |
| 2006/0167531 A1* | 7/2006 | Gertner | A61N 5/0603 607/86 |
| 2007/0179571 A1* | 8/2007 | De Taboada | A61N 5/0622 607/88 |
| 2007/0244526 A1* | 10/2007 | Zaghetto | A61N 5/0616 607/89 |
| 2009/0177125 A1 | 7/2009 | Pilcher et al. | |
| 2009/0270946 A1* | 10/2009 | Spivak | A61N 5/0614 607/54 |
| 2010/0106077 A1* | 4/2010 | Rabin | A61N 5/0616 604/20 |
| 2011/0197466 A1* | 8/2011 | Shami | A45D 20/12 34/283 |
| 2016/0129278 A1 | 5/2016 | Mayer | |

OTHER PUBLICATIONS

International Search Report including Written Opinion for Application No. PCT/EP2019/053984, dated May 14, 2019, pp. 1-15.

* cited by examiner

OPTICAL GUIDE FOR DIFFUSING LIGHT RADIATION, MODULE AND DEVICE FOR TRANSCUTANEOUS IRRADIATION, IN PARTICULAR TRANSCRANIAL IRRADIATION

CROSS-REFERENCE TO RELATED APPLICATIONS

The present application is a national phase entry under 35 U.S.C § 371 of International Application No. PCT/EP2019/053984 filed Feb. 18, 2019, which claims priority from European Application No. 18305162.2 filed Feb. 16, 2018, all of which are hereby incorporated herein by reference.

The invention lies within the field of optical guides ensuring the conduction and the diffusion of a light radiation, in particular through a surface.

The invention more particularly lies within the field of treatment by transcutaneous light irradiation.

The transcutaneous irradiation is a known technique by which a radiation of waves or particles is emitted on contact with the skin and penetrates deeply.

It is known as an application of this technique the photobiomodulation and the Low-Level Laser Therapy (LLLT) using laser diodes and/or light-emitting diodes (LEDs) and allowing to repair and regenerate damaged tissues. This technique consists in positioning a probe on the skin of a patient and carrying out the photonic emission for a given time at the level of the damaged tissue area. The probe, for example marketed by the company THOR, includes an emission head placed on the skin, a handle for holding the emission head and power cables connected to a control unit. The emission head is held in place by the practitioner throughout the session.

These transcutaneous irradiation techniques, in particular by phototherapy, also apply to the neurological and psychiatric treatments. This is then called transcranial irradiation. In this case, a light emission probe ranging from visible to infrared, of the type described above, is positioned and held on the surface of the patient's head by the practitioner. It is possible to act by this technique on neurological disorders in a therapeutic way to restore or improve the neurological and cognitive faculties, to stop the progression of neuropsychiatric disorders, like neurodegenerative diseases of the Alzheimer type, or to maintain a quality of life.

Another application of transcutaneous irradiation is oximetry. This technique consists of emitting red and infrared lights, and of measuring their absorption and/or reflection by the blood flow. In this context, the transcranial cerebral oximetry is known, which ensures the measurement of the oxygen cerebral saturation.

The application of these two techniques for which the irradiation is carried out on the surface of the patient's head requires an optimized diffusion of light radiation involving the least possible light loss. The optical guides conventionally used include a planar emission surface. But when the diffusion is carried out on the surface of the skull, the hair forms a barrier which impedes the diffusion of light radiation through the scalp. One solution consists in shaving the patient locally, which has obvious drawbacks.

The invention mainly relates to an optical guide for diffusing light radiation which allows overcoming the aforementioned drawbacks.

The invention also relates to an optical guide able to adapt to the non-planar configuration of the surface to be irradiated, for example areas covered with the hair of a patient such as the surface of the scalp of a patient, or the pubis. The invention also applies to areas devoid of hair.

The invention further relates to a transcutaneous irradiation module and a transcutaneous and transcranial irradiation device ensuring the accurate, efficient and controlled diffusion of the light radiation to optimize the diffusion of the light radiations towards one or more target areas, in particular for neurological and psychiatric treatments.

To this end, the optical guide for diffusing light radiation through a surface of the invention is essentially characterized in that it includes a base comprising or able to hold at least one diffusion rod whose lower diffusion end protrudes from said base and is intended to be applied on or near said surface, and whose upper collecting end is intended to be located near and opposite (i.e. facing) a power supplied light source, and in that the diffusion rod is made of a material able to transmit light from its collecting end up to its diffusion end.

The optical guide may also include the following optional characteristics considered separately or according to all the possible technical combinations:

- the collecting end of the diffusion rod includes a converging or diverging lens.
- the lower diffusion end is planar.
- the base is made of a material able to transmit light.
- the base includes a plurality of through orifices through each of which a removable diffusion rod is housed.
- the optical guide is made in one piece integrating the diffusion rod(s).
- the diffusion rod is made of polymethyl methacrylate (PMMA) or of glass, or of polycarbonate or of transparent copolyester (PETG) or any other equivalent material with high transparency.

The invention also relates to a transcutaneous irradiation module which is essentially characterized in that it includes an optical guide as defined above, which guide is mounted in an annular casing including at least one power supplied light source located opposite and near the collecting end of a diffusion rod.

The module can also include the following optional characteristics considered separately or according to all possible technical combinations:

- the module includes a plurality of light sources, each of the light sources being located opposite and near the lower end of a diffusion rod.
- the light source includes an infrared laser diode or an infrared spectrum-emitting light-emitting diode (LEDs), or a red spectrum-emitting light-emitting diode (LEDs).
- the module includes a plurality of light sources comprising at least one infrared laser diode, and/or an infrared spectrum-emitting light-emitting diode, and/or a red spectrum-emitting light-emitting diode and in that it includes a plurality of diffusion rods, each diffusion rod being associated with a light source.
- the infrared laser diode is of the pulsed type.
- the pulsed-type laser diode emits in the infrared at a wavelength between 700 and 1,200 nanometers, has a pulse duration between 20 and 200 nanoseconds, a pulse train between 1 and 10 kHz, preferably between 1 and 20 kHz, typically 15 kHz and a pulse power between 0.5 and 12 Watts.
- the modulation frequency applied to the light-emitting diodes and to the infrared laser is between 1 and 1,000 Hz.

The invention further relates to a transcutaneous and transcranial irradiation device which is essentially characterized in that it includes positioning means on the head of a user and at least one ring made of an elastic and/or flexible material and able to ensure the attachment by elastic grip of an irradiation module as previously described.

Preferably, the device includes a plurality of rings connected together by junction elements and the rings are symmetrically disposed on either side of an axis coincident with the median axis of the head when the device is in place on the head of the user, the rings include peripheral rings, at least some of which are not connected together by junction elements.

The invention finally relates to the use of the optical guide, as previously described, for diffusing a light radiation through the scalp of a user.

Figure 2:
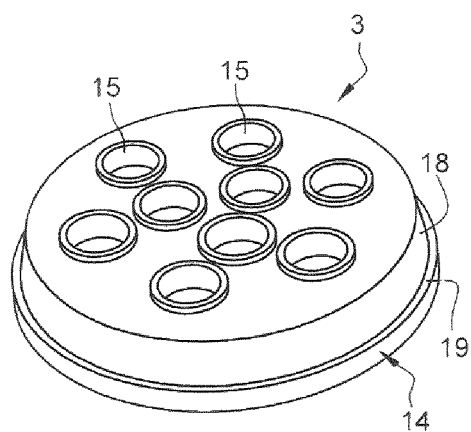
Figure 3:
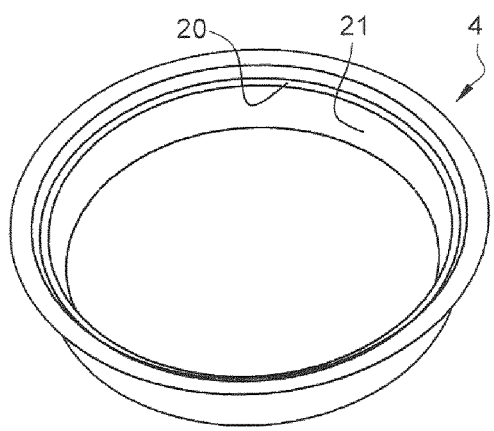
Figure 4:
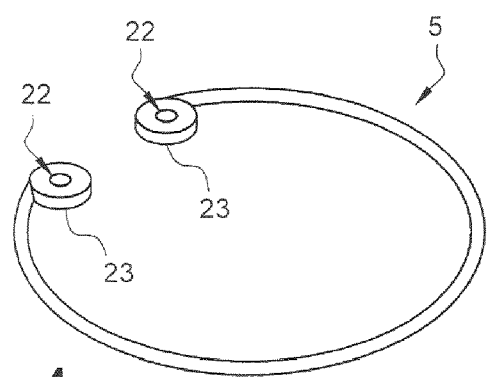
Figure 5:
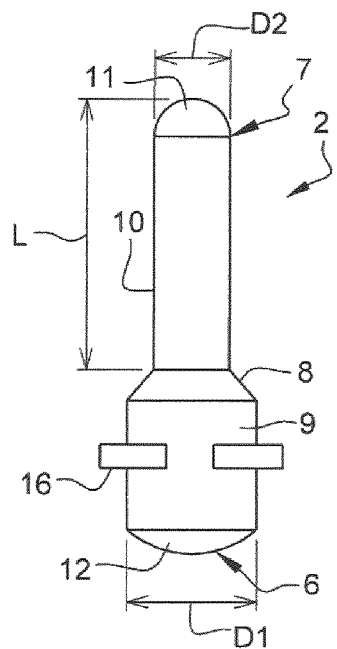
Figure 5A:
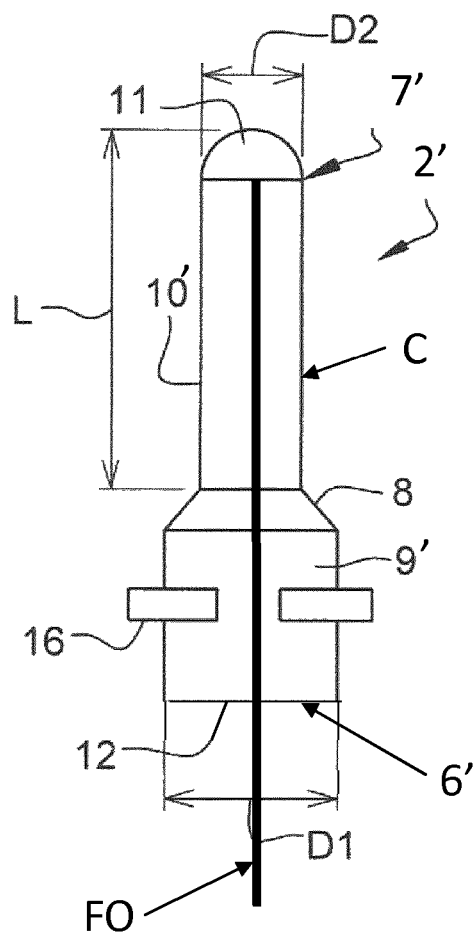
Figure 6:
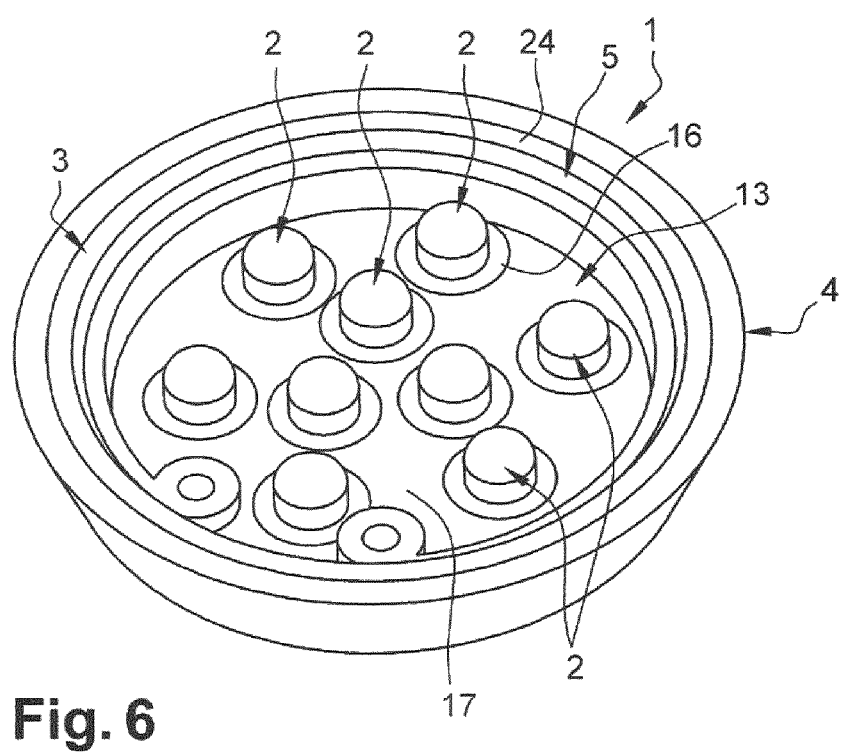
Figure 7:
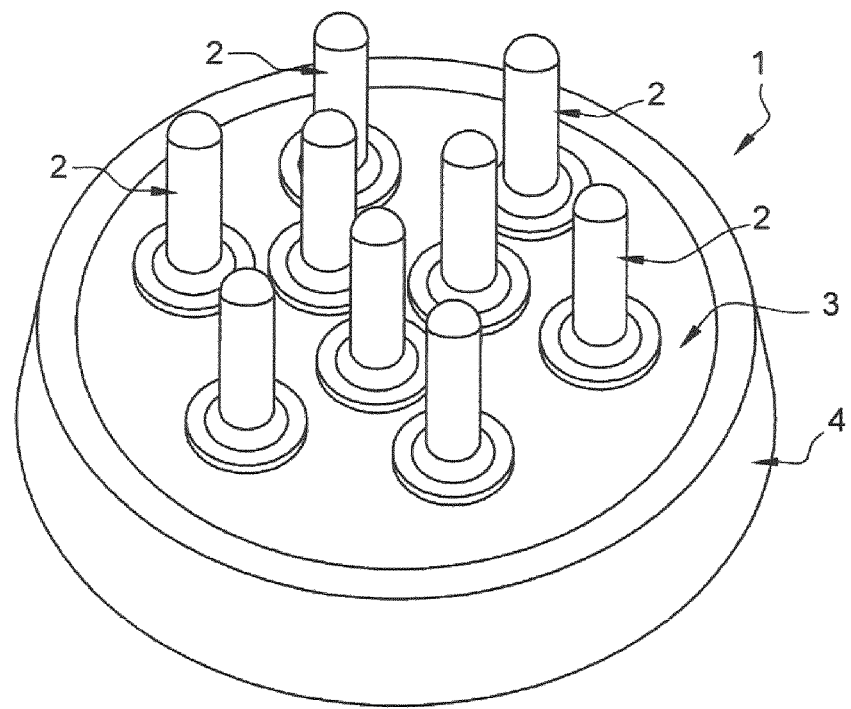
Figure 8:
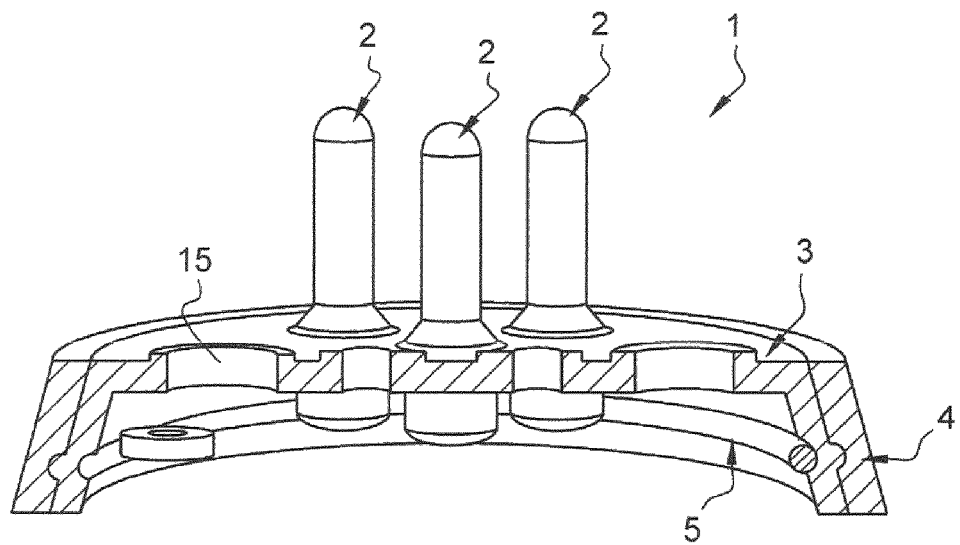
Figure 9:
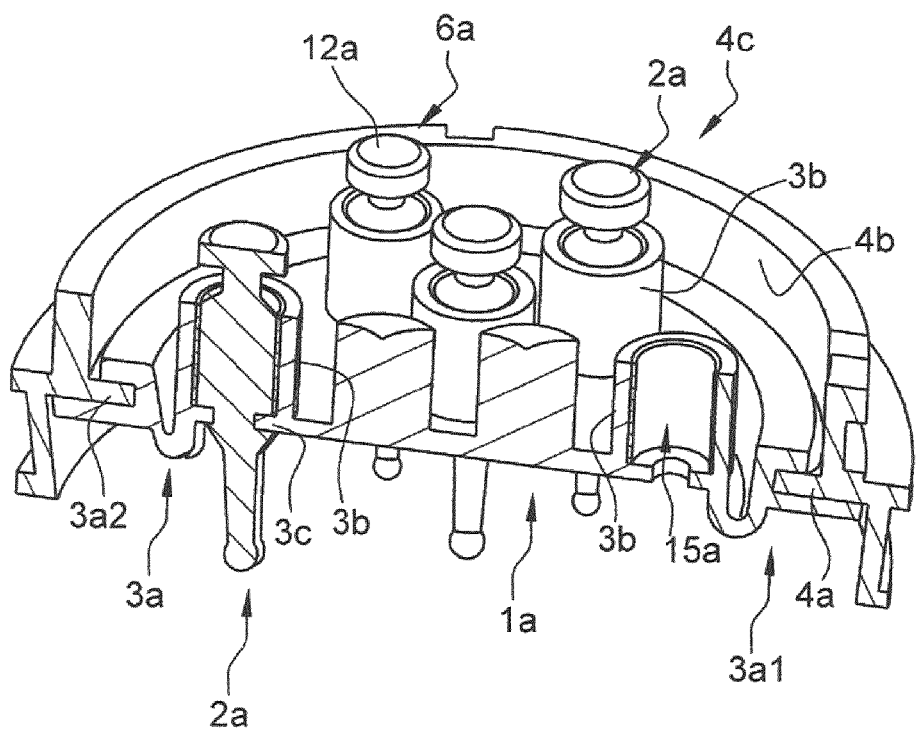
Figure 10:
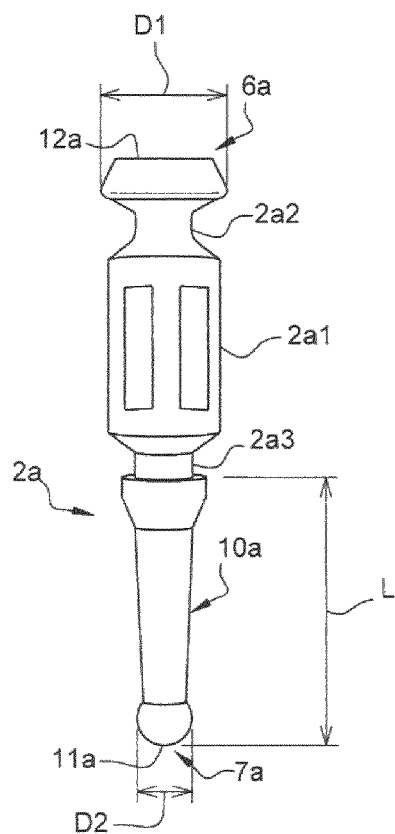
Figure 11:
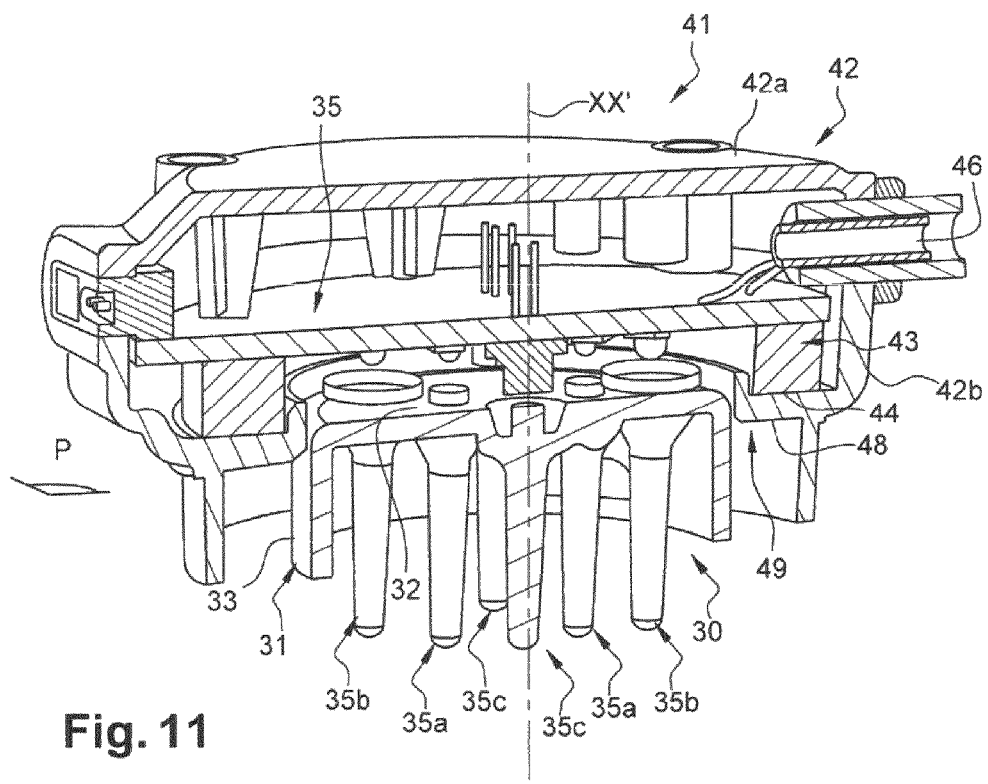
Figure 12:
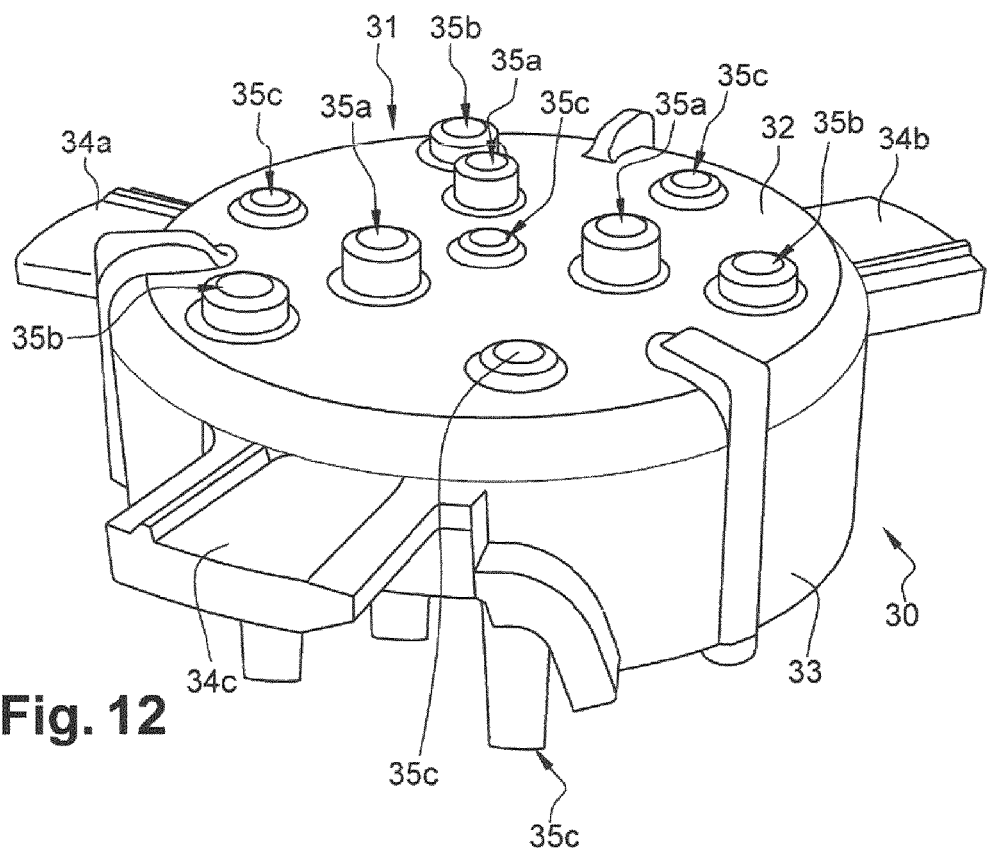
Figure 13:
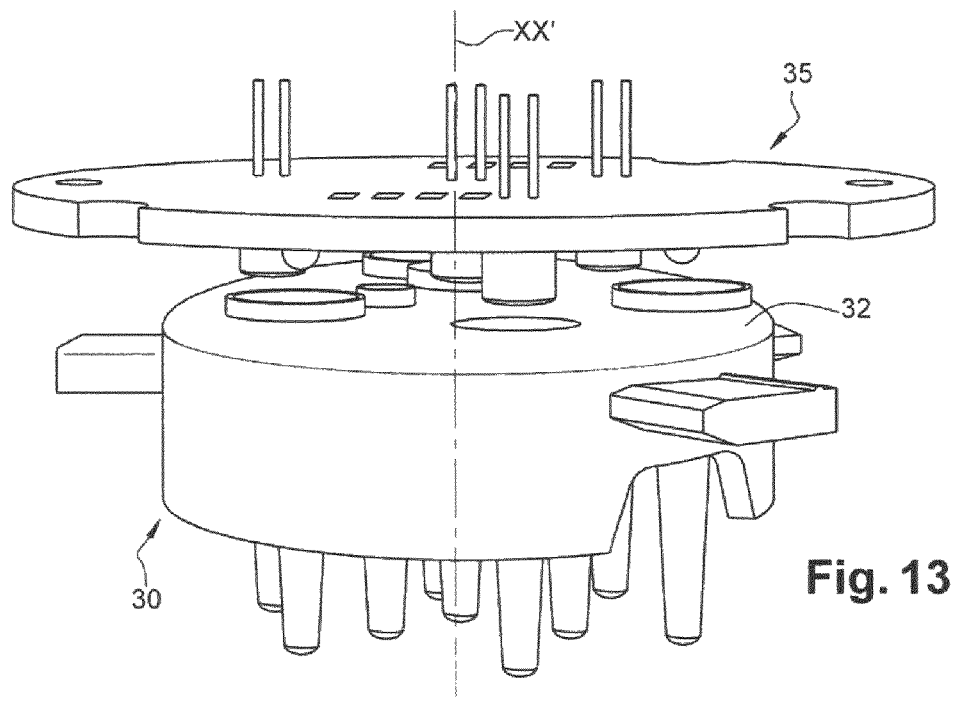
Figure 14:
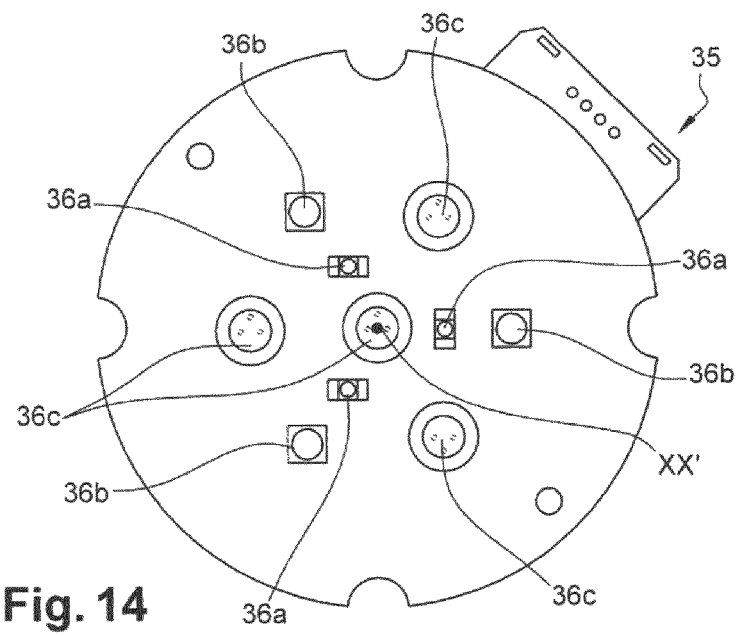
Figure 15:
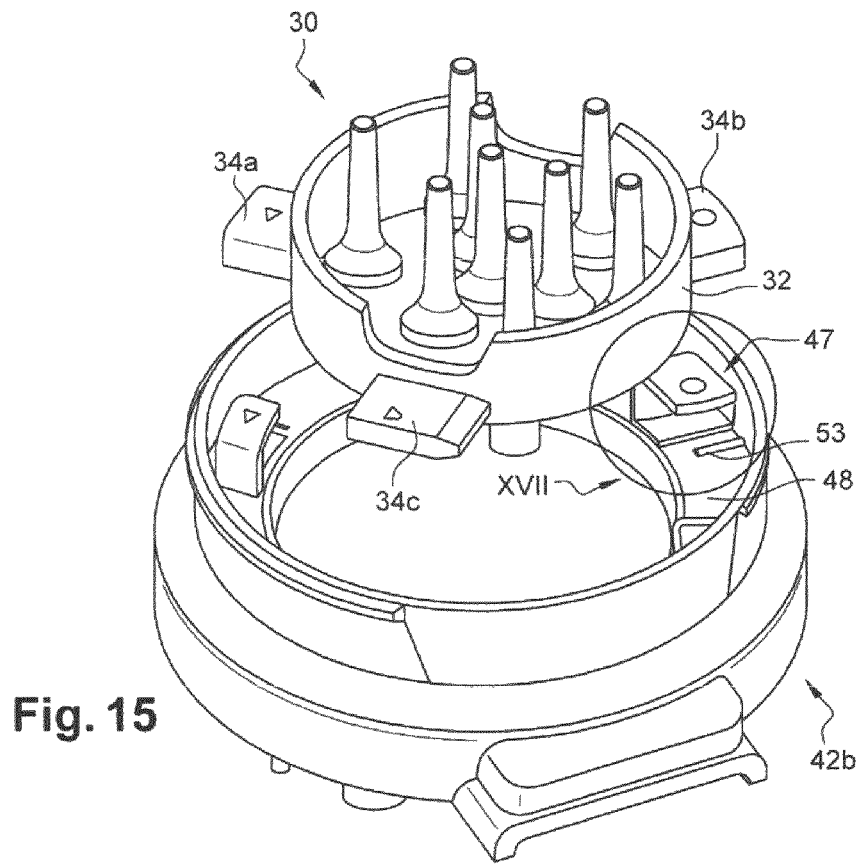
Figure 16:
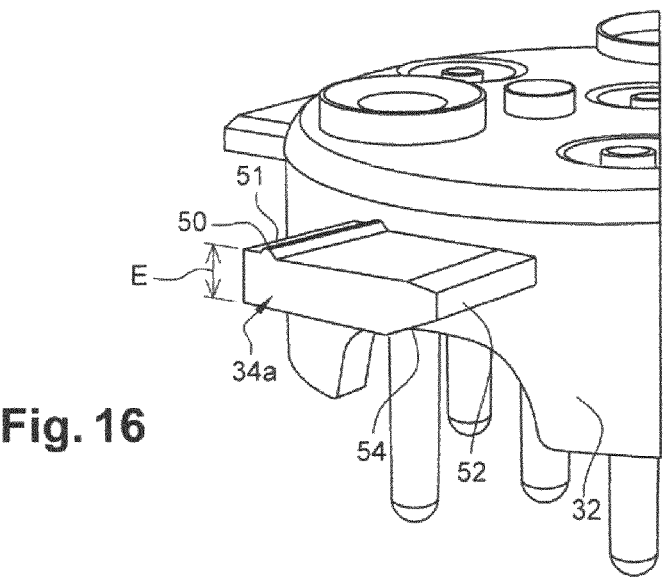
Figure 17:
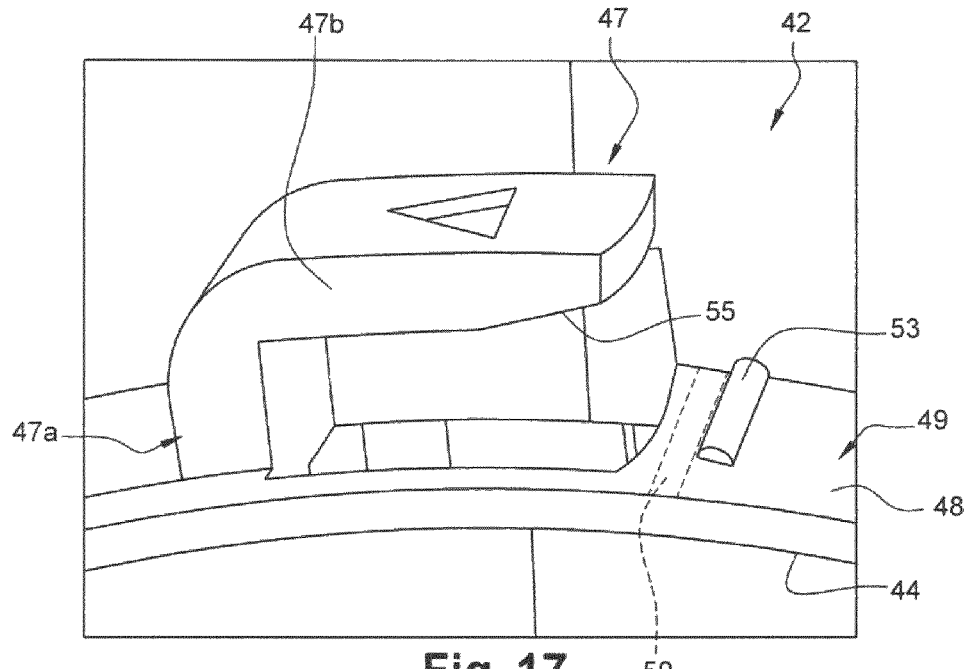
Figures 18A, 18B, 18C:
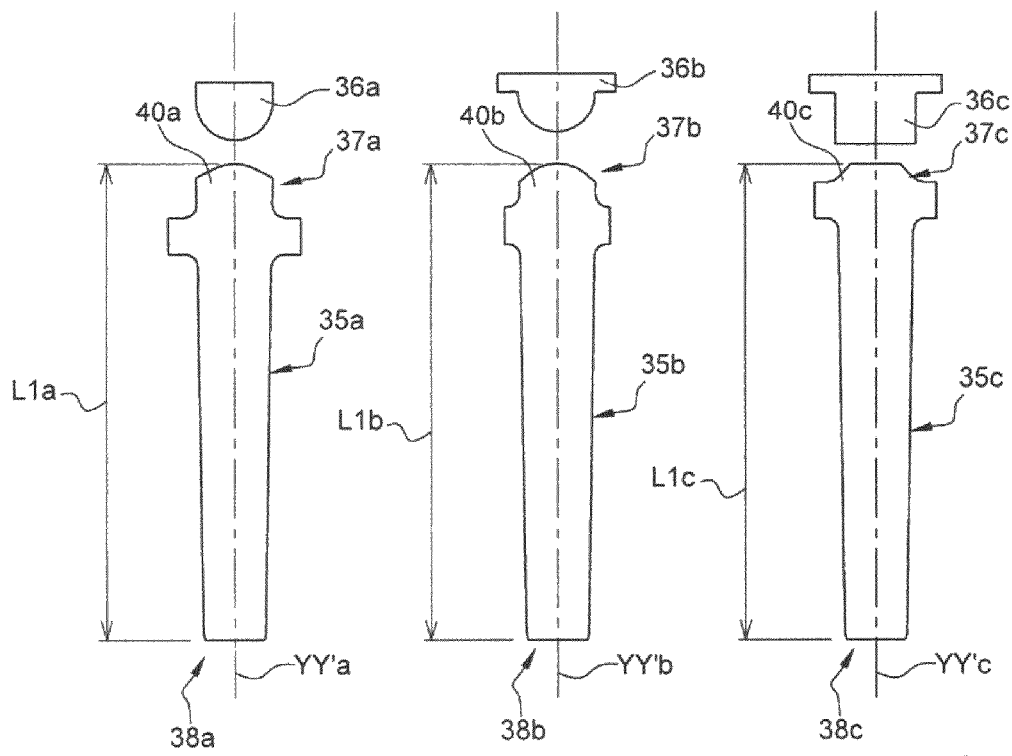

Other characteristics and advantages of the invention will emerge clearly from the description which is given below, for indication and without limitation, with reference to the appended figures among which:

FIGS. 1 and 2 are schematic perspective representations of the base of the optical guide of the invention according to a first variant of the invention respectively from its inner face (FIG. 1) located on the side of the light sources and from its outer face (FIG. 2) located on the side of the surface to be irradiated, FIG. 3 is a schematic perspective representation of the annular casing of the optical guide of the invention according to the first variant intended to surround the optical guide to ensure in particular its rigidity, FIG. 4 is a schematic perspective representation of an elastic ring ensuring the securing of the base of the optical guide according to the first variant of FIGS. 1 and 2 and of the annular casing of FIG. 3, FIG. 5 is a schematic representation of a diffusion rod intended to be mounted on the base of the optical guide according to the first variant of FIGS. 1 and 2, FIG. 5a is a schematic representation of a diffusion rod consisting of two parts;

FIG. 6 is a schematic perspective representation of the lower face on the side of the light sources of the optical guide of the invention according to the first variant including diffusion rods mounted on the base, which base is secured to the annular casing in particular by means of the elastic ring, FIG. 7 is a schematic perspective representation of the optical guide of the invention of FIG. 6 according to the first variant from its outer face intended to be affixed to the surface to be irradiated, FIG. 8 is a schematic sectional representation of the optical guide of the invention according to the first variant of FIGS. 6 and 7, FIG. 9 is a schematic perspective and sectional representation of the optical guide of the invention according to a second variant and including a base and a plurality of diffusion rods mounted in said base, FIG. 10 is a schematic representation of a diffusion rod adapted to the optical guide of the invention according to the second variant of FIG. 9, FIG. 11 is a schematic perspective and sectional representation of a module of the invention integrating an optical guide according to a third variant of the invention, FIG. 12 is a schematic perspective representation of the optical guide of the invention according to the third variant, FIG. 13 is a schematic perspective representation of the optical guide of the invention according to the third variant represented surmounted by the electronic board which integrates the light sources directed towards the upper end of each of the diffusion rods, FIG. 14 is a top representation of the electronic board of the module of FIG. 11 illustrating the position of the light sources, FIG. 15 is an exploded perspective representation of the optical guide of the invention from its outer face on the side of the surface to be irradiated, and of the sleeve on which the optical guide is intended to be secured, FIG. 16 is a schematic perspective representation of a portion of the optical guide of the invention according to the third variant illustrating a fin forming a means for securing to the sleeve represented in FIG. 15, FIG. 17 is a schematic representation of the portion circled XVII in FIG. 15 and illustrating the retaining element on the sleeve of the fin of FIG. 16, FIGS. 18A, 18B and 18C are side representations of the diffusion rods respectively intended to ensure the light diffusion of an infrared-emitting light-emitting diode (LED) (FIG. 18A), of a red-emitting light-emitting diode (LED) (FIG. 18B) and of an infrared-emitting laser diode (FIG. 18C).

Figure 19:
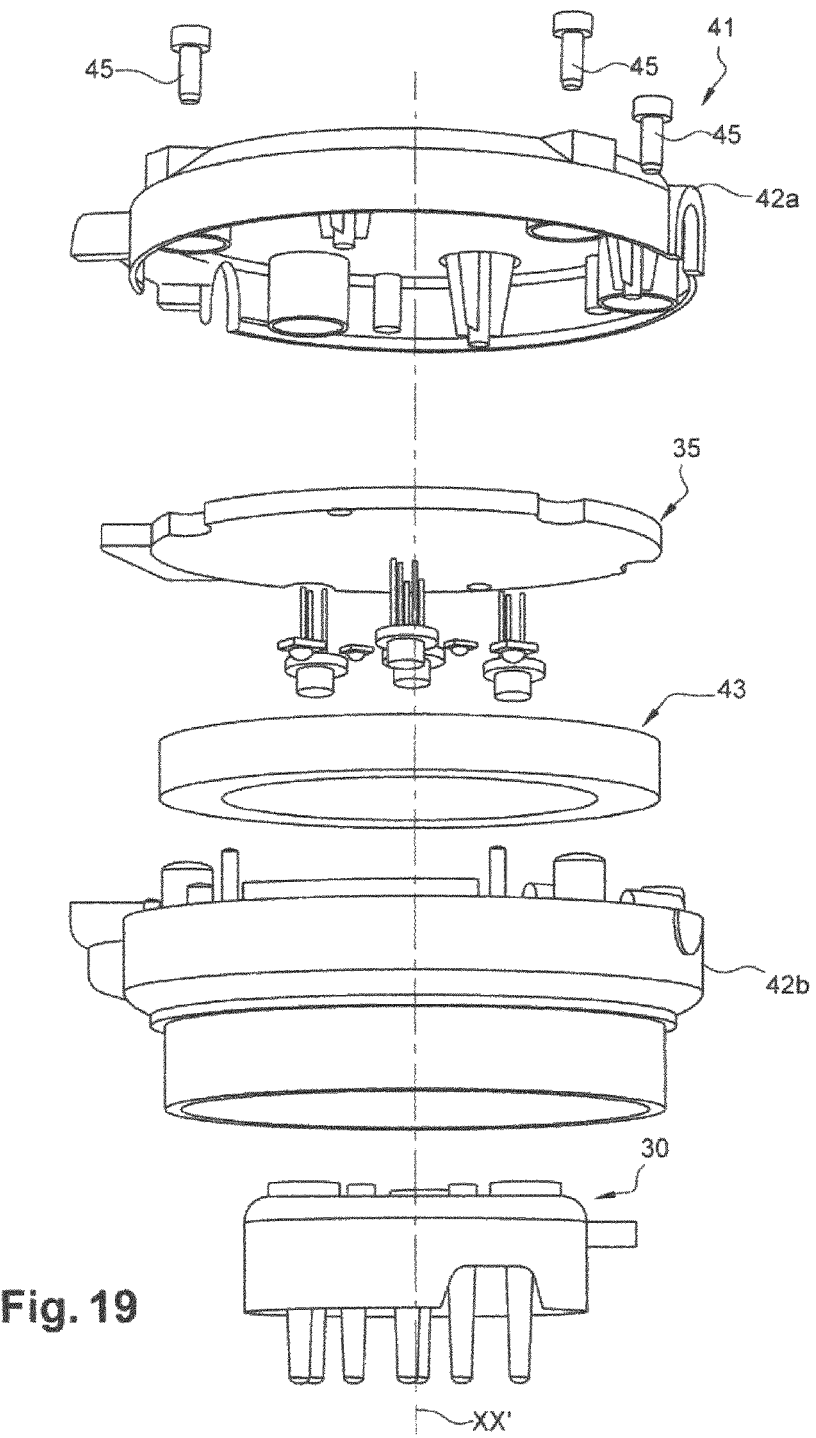
Figure 20:
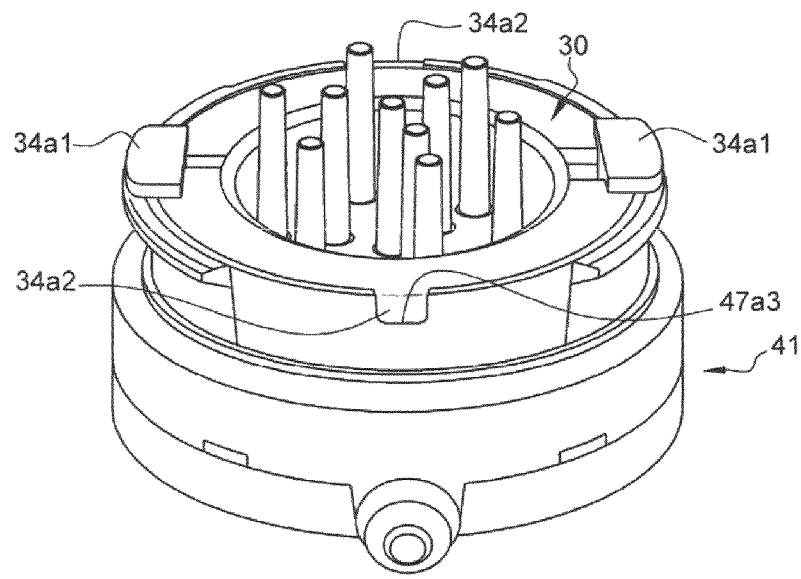
Figure 21:
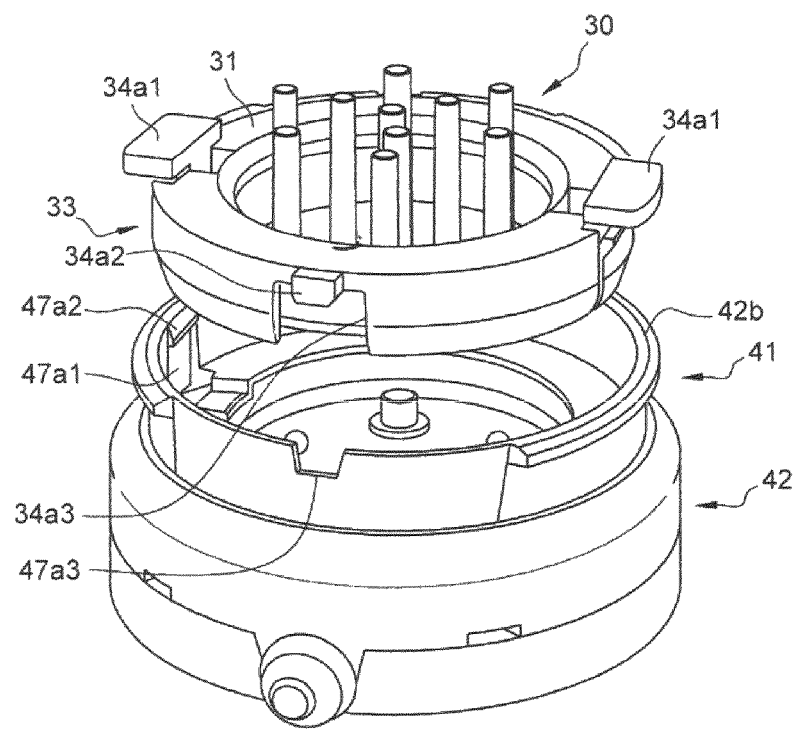
Figure 22:
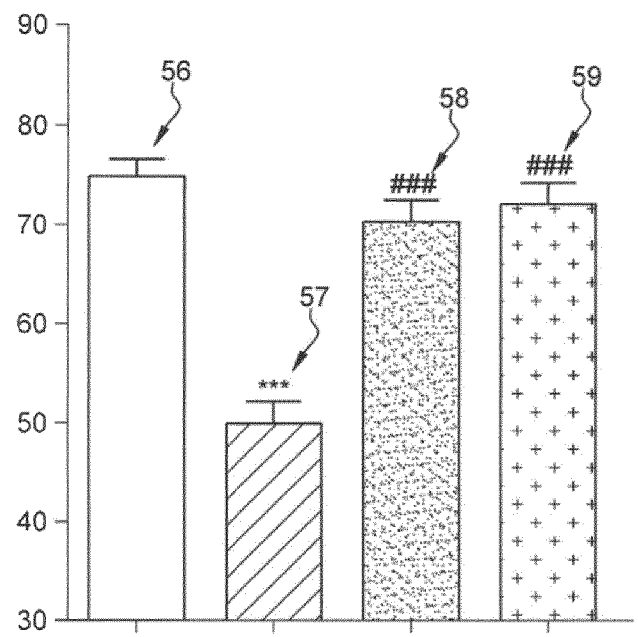
Figure 23:
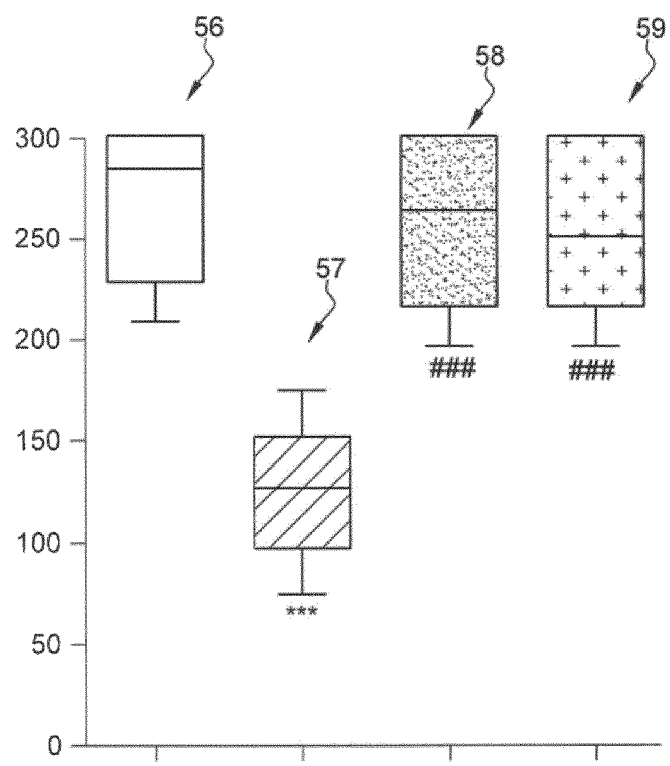
Figure 24:
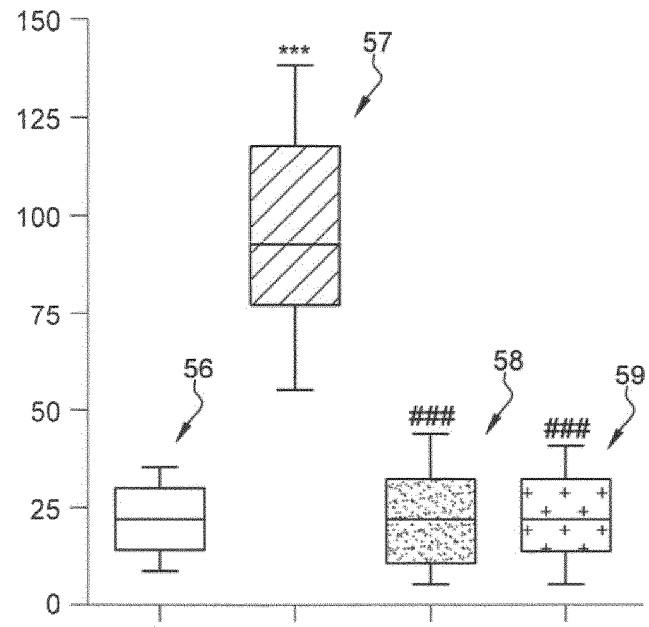
Figure 25:
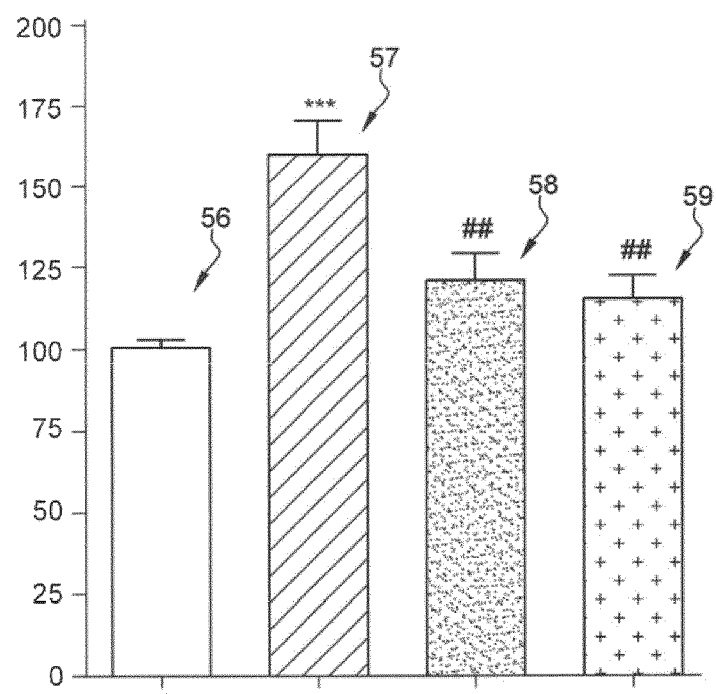
Figure 26:
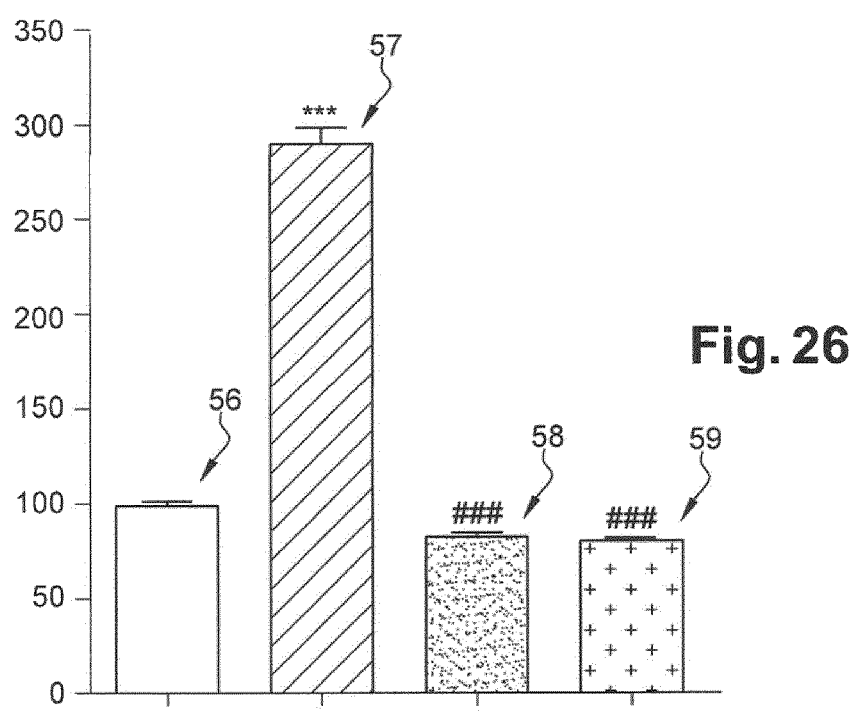
Figure 27:
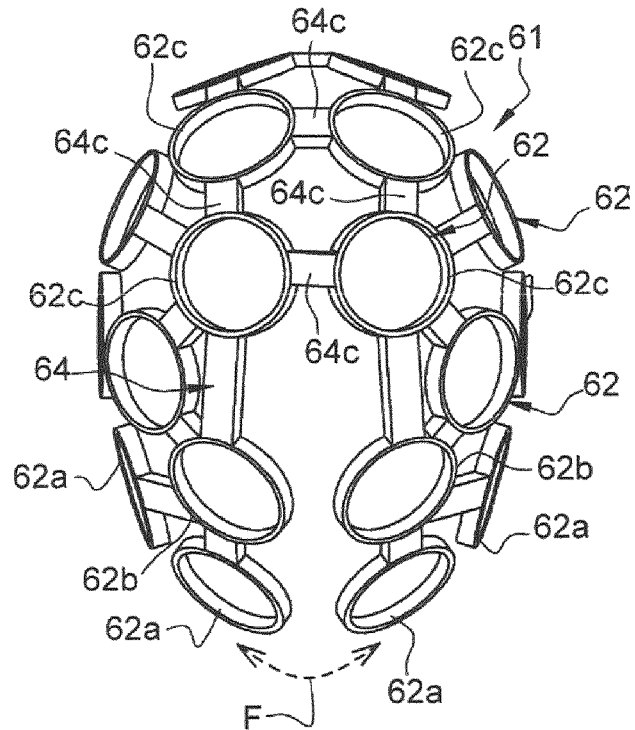
Figure 28:
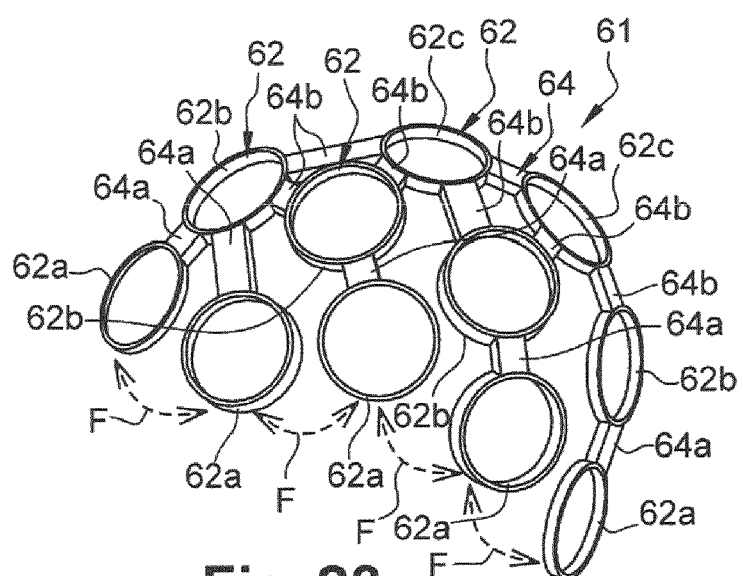
Figure 29:
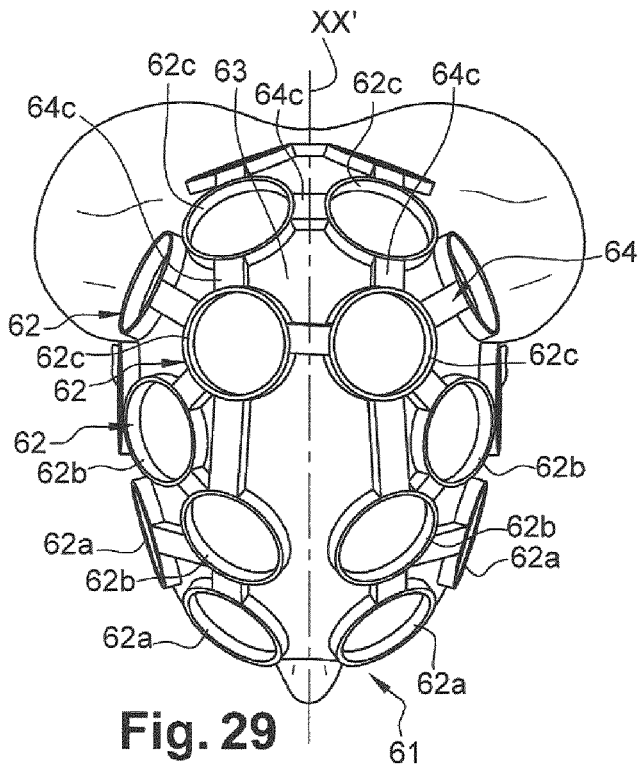
Figure 30:
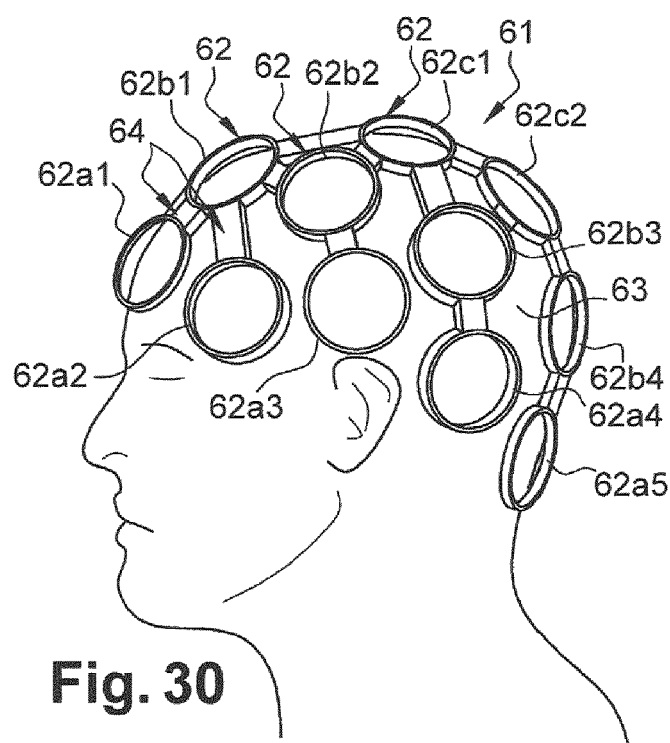
Figure 31:
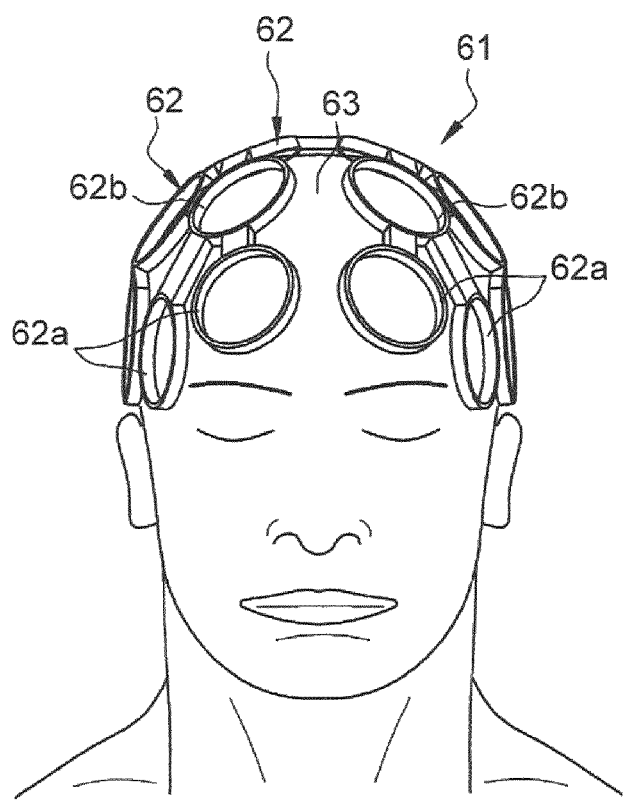
Figure 32:
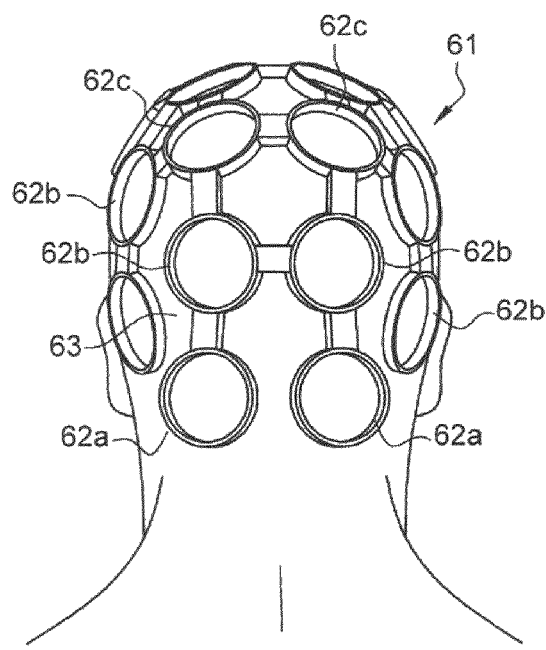
Figure 33:
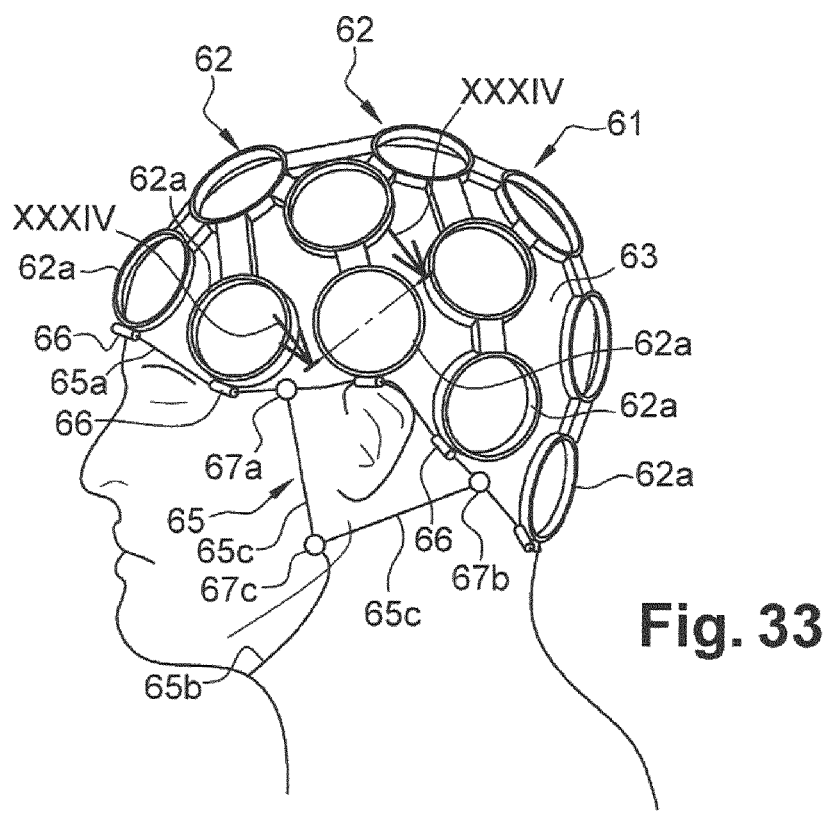
Figure 34:
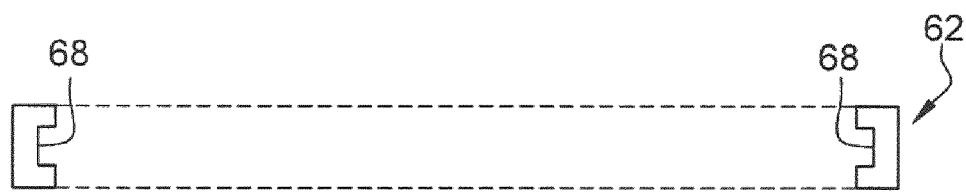
Figure 35:
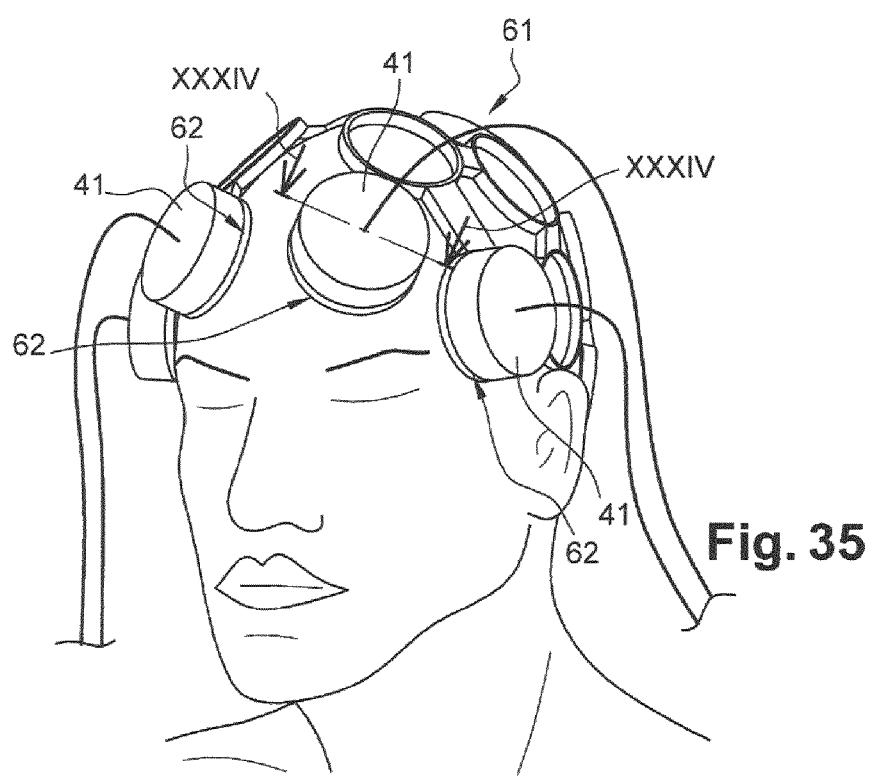

FIG. 19 is an exploded schematic representation of a module of the invention integrating the optical guide of the invention according to the third variant, FIG. 20 is a schematic perspective top representation of the module of the invention integrating an optical guide according to a fourth variant of the invention, FIG. 21 is an exploded schematic perspective top representation of the module of the invention integrating an optical guide according to a fourth variant of the invention, FIG. 22 is a diagram illustrating the alteration of the spontaneous spatial memory of mice to which the Aβ25-35 amyloid peptide has been injected, for shaved mice subjected to an irradiation treatment carried out with an irradiation module including a planar lens in other words a transparent plate, for unshaven mice subjected to an irradiation treatment carried out with an irradiation module including an optical guide according to the invention, and for control mice not subjected to an irradiation treatment, FIG. 23 is a diagram illustrating the alteration of the long-term spatial memory according to a first test of mice into which the Aβ25-35 amyloid peptide has been injected, for shaved mice subjected to an irradiation treatment carried out with an irradiation module including a planar lens, in other words a transparent plate, for unshaven mice subjected to an irradiation treatment carried out with an irradiation module including an optical guide according to the invention, and for control mice not subjected to an irradiation treatment, FIG. 24 is a diagram illustrating the alteration of the long-term spatial memory according to a second test of mice into which the Aβ25-35 amyloid peptide has been injected, for shaved mice subjected to an irradiation treatment carried out with an irradiation module including a planar lens, in other words a transparent plate, for unshaven mice subjected to an irradiation treatment carried out with an irradiation module including an optical guide according to the invention, and for control mice not subjected to an irradiation treatment, FIG. 25 is a diagram illustrating the level of lipid peroxidation in the hippocampus of mice into which the Aβ25-35 amyloid peptide has been injected, for shaved mice subjected to an irradiation treatment carried out with an irradiation module including a planar lens in other words a transparent plate, for unshaven mice subjected to an irradiation treatment carried out with an irradiation module including an optical guide according to the invention, and for control mice not subjected to an irradiation treatment, FIG. 26 is a diagram illustrating the level of TNFα (tumor necrosis factor) measured by the enzyme-linked immunosorbent assay ELISA in the hippocampus of mice into which the Aβ25-35 amyloid peptide has been injected, for shaved mice subjected to an irradiation treatment carried out with an irradiation module including a planar lens, in other words a transparent plate, for unshaven mice subjected to an irradiation treatment carried out with an irradiation module including an optical guide according to the invention, and for control mice not subjected to an irradiation treatment, FIG. 27 is a schematic top view of a support of irradiation modules intended to receive at least one module of the invention integrating the optical guide of the invention according to one of the first, second and third variants, FIG. 28 is a schematic side view of the irradiation module support, FIG. 29 is a schematic top view of the module support in position on the head of a user, FIG. 30 is a schematic side view of the module support in position on the head of a user, FIG. 31 is a schematic front view of the module support in position on the head of a user, FIG. 32 is a schematic back view of the module support on the head of a user, FIG. 33 is a schematic side view of the irradiation module support on which the strap for retaining said support is also illustrated, FIG. 34 is a sectional view along the line XXXII-XXXII of FIG. 33 of a ring of the module support provided with an inner groove, and FIG. 35 is a general perspective front view of the irradiation device of the invention including the irradiation module support and four modules in position in four rings located at the level of the frontal lobe.

In all of the figures, similar elements bear identical references.

The optical guide of the invention has one, or preferably several, light diffusion rod(s) intended to be affixed against the surface to be irradiated. The rods are advantageously made of a material transmitting light from a first end located near a light source up to the opposite end located near the surface to be irradiated. Alternatively, the rods may comprise a material transmitting light from a first end located near a light source up to the opposite end located near the surface to be irradiated. According to this alternative, an optical fiber made of material transmitting light can be disposed in a conduit. According to the first and second variants described below, the diffusion rods are independent parts mounted on the optical guide. According to the third variant, the optical guide is made in one piece by integrating the diffusion rods. In both cases, it involves ensuring the diffusion of the light radiation from the end of the rod on the side of the light sources, up to its opposite end on the side of the surface to be irradiated.

According to the first variant, each rod is mounted on a base by forming two full-fledged parts and thus constituting the optical guide. Thus, the light radiation which penetrates at the level of the first end of the rod is integrally conducted up to the opposite end without risk of loss of diffusion within the thickness of the base.

Preferably, each rod includes at its end located near the surface to be irradiated a converging lens ensuring the targeted diffusion of the light radiation.

Furthermore, in order not to lose the light radiation which does not penetrate at the level of the first end of the rod, the base is advantageously made of a material which also transmits light.

In addition, to adapt to the surface to be irradiated, for example when this surface is the scalp, the base is made of a flexible material. Thus, the base can conform to the configuration of the surface to be irradiated, while ensuring the surface contact of the rods with this surface.

Referring to FIGS. 1 to 8 to describe the elements constituting the optical guide of the invention according to the first variant.

Referring to FIGS. 6, 7 and 8, the optical guide of the invention 1 includes a plurality of diffusion rods 2 (in this example nine in number) mounted on a base 3, which base 3 is held in an annular casing 4 in particular by means of an elastic ring 5.

With reference to FIG. 5, according to one embodiment, each diffusion rod 2 is made in one piece and extends longitudinally from a first lower collecting end 6 intended to be located near a light source, up to an opposite diffusion end 7 intended to be affixed to the surface to be irradiated, for example the scalp of a user. To best ensure the collection of the light radiation generated by the light source (not represented in this figure), the diameter D1 of the collecting end 6 is greater than the diameter D2 of the diffusion end 7. The diffusion rod 2 includes longitudinally a frusto-conical setback 8 connecting the lower portion 9 of diameter D1 of the rod 2 to its upper portion 10 of diameter D2. For example, the diameter D1 is of 2 millimeters and the diameter D2 is of 1.5 millimeters.

The upper portion 10 of the rod 2 has a length L of between 3 and 15 millimeters, in this example, 10 millimeters. This length L must be sufficient for the diffusion end 7 to be in contact with the surface to be irradiated, even in the presence of a thickness of hair when the optical guide is used on the scalp, but must not be too long, otherwise the skin will be damaged.

The optimization of the collection and diffusion of the light radiation is ensured by the following independent parameters: the rod 2 is made of a material which effectively diffuses the light, in this example polymethyl methacrylate (PMMA), or glass, or polycarbonate or transparent copolyester (PETG) or any other equivalent material with high transparency. In addition, the diffusion end 7 of the rod 2 includes a converging lens 11 which accurately conducts the light towards the intended target. Finally, the collecting end 6 also includes a converging lens 12 making it possible to efficiently collect the light radiation derived from the corresponding light source which is disposed near this collecting end 6.

The diffusion rod 2 is mounted on the base 3 which is composed of a circular planar membrane 13 and of an annular peripheral rim 14. The base 3 is made in this example of a flexible transparent material, for example of silicone. For example, the base 3 has a diameter of 40 millimeters, a height of 5 millimeters and a thickness of 1.7 millimeters. The circular membrane 13 includes through orifices 15 (FIGS. 1 and 2) through which the rods 2 are forcefully inserted and held by elastic friction. To reinforce the holding of the rods 2 in the orifices 15 and particularly to prevent the rods 2 from being extracted from the orifices 15 on the side of the skin, the lower portion 9 of the rod 2 (FIG. 5) includes a circular protruding abutment 16 which bears (FIG. 6) against the inner face 17 of the circular base 13 of the support membrane 3. Thus, the rods 2 are firmly held on the support membrane 3.

Referring to FIG. 2, the outer face 18 of the peripheral rim 14 of the base 3 includes a circular rib 19 intended to be housed in a corresponding circular groove 20 arranged on the inner face 21 of the annular casing 4. This annular casing 4 is made of a material more rigid than the support membrane, for example of polycarbonate or metal. Thus, and as seen for example in FIG. 6, the annular casing 4 surrounds the support plate 3 at its peripheral edge 14 by giving the optical guide 1 a rigidity allowing this guide 1 to be integrated in a module as will be described later.

To reinforce the securing of the support plate 3 to the annular casing 4, there is provided an elastic ring 5 (FIG. 4) also known as "circlip" which has a generally annular open shape while including two ends 22 located nearby and each having a prominence 23 which allows to manually bring the two ends 22 together until contact to reduce the diameter of the elastic ring 5 and allow its insertion and removal.

The elastic ring 5 is mounted at the inner face 24 of the peripheral edge 14 of the base 3, and in a circular groove 25 arranged on this inner face 24. The elasticity of the ring 5 pushes back the peripheral edge 14 of the base 3 against the circular casing 4 (FIG. 6) by reinforcing the securing of the base 3 and of the annular casing 4.

The number and positioning of the diffusion rods correspond to the number and positioning of the light sources. As seen in FIG. 1, nine through orifices 15, and therefore nine associated diffusion rods 2, are provided in this example. The nine orifices 15 (and thus the nine rods 2) are distributed around the center O of the circular membrane 13 with three central orifices and five peripheral orifices, all evenly circularly distributed.

In the example described above, the optical guide 1 is affixed to the scalp of a user and used to expose some areas of the brain to electromagnetic radiations ranging from the visible spectrum to the infrared. This type of exposure will be applied to the neurological and/or psychiatric treatments, for example the neurodegenerative pathologies of the Alzheimer type. It will be also possible to use the optical guide to make transcranial brain oximetry measurements. In this case, some diffusion lenses 11 of each rod 2 will then act as radiation diffusers, and other diffusion lenses 11 of each rod 2 will act as collectors.

Referring to FIGS. 9 and 10 and according to the second variant of the invention, the base 3a has a substantially circular shape and includes a peripheral edge 3a1 made of two substantially parallel portions and delimiting a groove 3a2 for receiving a coincident rib 4a made on the annular inner face 4b of the annular casing 4c. This annular casing 4c differs somewhat structurally from the annular casing 4 of the first variant but is meant to have the same functionality of holding the optical guide 1a in an irradiation module.

In this variant, it is provided that the diffusion rods 2a, seven in number in this example, are held in position on the base 3a by means of sleeves 3b forming part of the base 3 and enclosing the associated rod 2a when the latter is press-fitted into the sleeve 3b. To this end, the base 3 is made of a sufficiently flexible material so that the diffusion rods 2a can be press-fitted into the corresponding sleeves 3b, and the material constituting the inner face of each sleeve 3b has a coefficient of friction such that it participates in maintaining the diffusion rods 2a on the base 3a. Preferably, the base 3 is made in one piece and therefore has a uniform coefficient of friction which also allows it to hold the rib 4a of the annular casing 4c in the corresponding circular groove 3a2 of the base 3a.

The diffusion rod 2a has in this variant a structural adaptation to the presence of the sleeves 3b. As such and more particularly with reference to FIG. 10, each diffusion rod 2a has an essentially tubular attachment portion 2a1 and whose diameter and length are adapted to the diameter and the length of the sleeves 3b of the base 3a. This attachment portion 2a1 is delimited by an upper shoulder 2a2 on the side of the collecting end 6a and a lower shoulder 2a3 on the side of the opposite diffusion end 7a. This second shoulder 2a3 also forms a means for holding the rod 2a on the base 3a since this shoulder 2a3 is in cooperation with a rib 3c (FIG. 9) made in the lower portion of the associated sleeve 3a.

It will also be noted that, unlike the diffusion rod 2 of the first variant, the diffusion rods 2a of the guide of the second variant has at its collecting end 6a a diverging lens 12a intended to be located near the associated light source (not represented) and to adapt to the diffusion radius of this light source by best ensuring the diffusion of the light radiation from the collecting end 6a up to the diffusion end 7 which includes, as for the first variant, a converging lens IIa.

As for the first variant, to best ensure the collection of the light radiation generated by the light source, the diameter D1 of the collecting end 6a is greater than the diameter D2 of the diffusion end 7a. The length L of the upper portion 10a of the rod 2a which emerges from the base 3 in the direction of the surface to be irradiated must be sufficient for the diffusion end 7a to be in contact with the surface to be irradiated, even in the presence of a thickness of hair when the optical guide is used on the scalp, but must not be too long, otherwise the skin will be damaged.

As for the first variant, the diffusion rod 2a is made of a material which effectively diffuses light, in this example of polymethyl methacrylate (PMMA), or of glass, or of polycarbonate or of transparent copolyester (PETG) or any other equivalent material with high transparency.

Referring now to FIGS. 11 to 19 to describe a module of the invention integrating the third variant of the optical guide of the invention in which the guide is made in one piece.

Referring to FIGS. 11 and 12, the optical guide 30 of the third variant comprises a base 31 made of a circular planar face 32 which is extended by an annular skirt 33 from which three fins 34a, 34b, 34c diametrically protrude outwardly, intended to form means for securing the optical guide 30 to the module of the invention 41 as will be described later. The optical guide 30 includes ten diffusion rods divided into three groups 35a, 35b, 35c according to the light source 36a, 36b, 36c associated therewith.

As illustrated in FIGS. 11 and 13, the planar face 32 of the optical guide 30 is intended to be arranged in the module opposite and near an electronic board 35 including a plurality of light sources protruding from the electronic board 35 parallel to the main axis XX' of the electronic board 35 and of the module, towards the optical guide 30 and coaxially with the associated diffusion rods 35a, 35b, 35c.

The light sources are also divided into three groups, namely (FIG. 14):
three light-emitting diodes (LEDs) 36a which are infrared-emitting at a wavelength between 700 and 1,200 nanometers, preferably 850 nanometers. The three infrared LEDs 36a are circularly and evenly distributed about and near the main axis XX' of the electronic board 35 and of the module,
three light-emitting diodes (LEDs) 36b which are red-emitting at a wavelength between 600 and 700 nanometers, preferably at 625 nanometers. The three red LEDs 36b are circularly and evenly distributed about and at a greater distance than the infrared LEDs from the main axis XX', and
four pulsed-type lasers 36c which are infrared-emitting at a wavelength between 700 and 1,200 nanometers preferably at 850 nanometers. Each of these lasers has pulse duration between 20 and 200 nanoseconds, a pulse train between 1 and 10 kHz, preferably between 1 and 20 kHz, typically 15 kHz and a pulse power between 0.5 and 12 Watts, preferably between 1 and 6 Watts included. A first laser 14s is centered on the axis XX' and the three other lasers are circularly and evenly distributed about and at a greater distance than the infrared LEDs from the main axis XX', on the same circumference as the red LEDs 36b. It is alternatively possible to provide three pulsed lasers 14a which will be circularly and evenly distributed about the axis XX'. It is also alternately possible to provide less than three lasers, for example a single pulsed laser centered on the axis XX'.

The overall modulation frequency applied to the light-emitting diodes and to the pulsed lasers is between 0 and 4,000 Hz, preferably between 1 and 1,000 Hz, preferably 10 Hz.

Referring to FIGS. 18A, 18B and 18C, each diffusion rod 35a, 35b, 35c extends longitudinally along its associated axis YY'a, YY'b, YY'c from a first lower collecting end 37a, 37b, 37c located proximally and coaxially opposite the associated light source 36a, 36b, 36c up to an opposite diffusion end 38a, 38b, 38c intended to be affixed to the surface to be irradiated, for example the scalp of a user. In this variant, the diffusion end 38a, 38b, 38c is planar to provide comfort to the user on the scalp from which the diffusion end 38a, 38b, 38c is affixed. Each diffusion rod 35a, 35b, 35c is of substantially conical shape from its collecting end 37a, 37b, 37c up to its diffusion end 38a, 38b, 38c.

The optimization of the collection and distribution of the light radiation is ensured by the following independent parameters. In particular, each diffusion rod 35a, 35b, 35c is made of a material that effectively diffuses light, for example of polymethyl methacrylate (PMMA), or of glass, or of polycarbonate or of transparent copolyester (PETG) or any other equivalent material with high transparency.

Regarding the infrared and red emissions, the diffusion rods 35a, 35b associated respectively with the infrared-emitting 36a and red-emitting 36b light-emitting diodes each include a collecting end 37a, 37b comprising a converging lens 40a, 40b which accurately conducts the light in the direction of the associated diffusion end 38a, 38b.

Furthermore, the length L1a, L1b of the diffusion rods 35a, 35b is adjusted to the focal distance of the associated converging lens 40a, 40b so that at least 40%, preferably at least 60%, of the total light emission emitted by the red and infrared LEDs starting, for example, from a diffusion angle of about 120°, reach the corresponding planar diffusion end 38a, 38b. With reference to FIG. 18c, the diffusion rod 35c associated with the laser 36c includes a planar lens 40c (in other words a transparent plate) positioned perpendicular to the laser beam whose diffusion radius coincides with the axis YYc'. This perpendicular positioning ensures the propagation in a straight line of the laser beam from the source 36c up to the diffusion end 38c. The distance between the collecting end 37c of the diffusion rod 35c and the laser 36c is between 1 and 3 millimeters, preferably 2 millimeters.

For example and to meet the criteria defined above, each diffusion rod 35a, 35b, 35c has a length L1a, L1b, L1c of between 17 and 18 millimeters, a larger diameter on the side of the collecting end 37a, 37b, 37c of about 3 millimeters, and a smaller diameter on the side of the planar diffusion end 38a, 38b, 38c of between 2.2 and 2.4 millimeters. Thus, all or most (more than 40%) of the light radiations emitted by the infrared LEDs 36a, the red LEDs 36b and the lasers 36c are diffused in the diffusion rods 35a, 35b, 35c towards the associated collecting ends 38a, 38b, 38c.

Referring to FIGS. 11 and 19, the optical guide 30 of the invention is arranged in a module 41 which includes an annular casing 42 made of an upper cover 42a and of a lower cover 42b securely held by a screwing by means of four screws 43, three of which are seen in FIG. 19. The casing 42 ensures in particular the coaxial holding of the optical guide 30 and of the electronic board 35 including the light sources 36a, 36b, 36c. In this variant, an annular magnet 43 is also present between the electronic board 35 and the optical guide 30 and generates a static magnetic field of between 50 and 300 milliTeslas. The magnet 43 is housed in a circular groove 44 which is arranged on the upper face of an annular edge 49 of the lower cover 42b of the casing 42 and which surrounds the optical guide 30. Thus, the light radiations generated by the light sources 36a, 36b, 36c extend perpendicular to the plane P of the magnet 43 and inside this magnet 43. Remaining within the scope of the invention, the module 41 does not include a magnet.

The electronic board 35 has a diameter at least equal to the diameter of the magnet 43 and rests on the magnet 43 while being secured to the upper cover 42a of the casing 42 by a screwing system or snapping not represented on the figures. The electronic board 35 is power supplied via an electric cable 46 (FIG. 11) which extends outside the module 41. The electric cable 46 also contains data wires (for example of the CAN bus or RS485 serial type), a wire for powering the irradiation source(s), one or more ground wire(s) and can be shielded.

As seen in the exploded view of FIG. 19, the main components of module 41 (casing 42, electronic board 35, magnet 43 and optical guide 30) are coaxially arranged about the main axis XX' of the module 41.

The securing between the optical guide 30 and the lower cover 42b of the cover 42, as well as the means associated with this securing are described with reference to FIGS. 15 to 17.

The three fins 34a, 34b, 34c evenly distributed protruding on the skirt 33 of the base 33 of the optical guide 30 are intended to engage in a grip member 47 arranged on the lower face 48 of the annular edge 49 of the lower cover 42b of the casing 42, whose upper face 44 forms a groove for receiving the magnet 43. The grip member 47 is L-shaped with a first portion 47a forming an abutment of the corresponding fin 34a, 34b, 34c and a second portion 47b substantially perpendicular to the first portion 47a and extending parallel to the lower face 48 of the annular edge 49 at a distance from this face 48 which coincides with the thickness E of the fin 34a, 34b, 34c to allow the grip of the fin 34a, 34b, 34c in the grip member 47.

In addition, as seen in FIG. 16, each fin 34a has a boss 50 arranged over the entire width of the fin 34a near its free end 51 opposite the free end 52 intended to come into abutment in the grip member 47. This boss 50 coincides with another boss 53 arranged over all or part of the width of the lower face 48 of the annular edge 49 of the lower cover 42 so that when the fin 34a is housed in the grip member 74, the boss 50 of the fin 34a is located downstream of the boss 53 (as illustrated in dotted lines in FIG. 17). The holding of the fin 34a in the grip member 47 is thus ensured.

Finally, to facilitate the insertion of the fin 34a into the grip member 47, the lower face of the fin 34a has a bevel 54 at the free end 52 intended to come into abutment in the grip member, which coincides with a bevel 55 arranged on the lower face of the second portion 47b of the grip member 47.

The optical guide of the invention according to the fourth variant of the invention presents an alternative to the means for securing the optical guide 30 to the module of the invention 41. These securing means include two snap-in tabs 34a1 arranged at the level of the base 31 of the optical guide 30 while being diametrically opposite and extending at the level of the annular skirt 33. Each snap-in tab 34a1 coincides with a housing 47a1 arranged at the level of the inner face of the lower cover 42b of the casing 42, which housing 47a1 includes a boss 47a2 which prevents the removal of the optical guide 30 from the module 41 when the optical guide is housed in the casing 42 and when by elastic return, the snap-in tabs 34a1 come into bearing contact against the inner face of the lower cover 42b. It is understood that the removal of the optical guide 30 from the module 41 is done by a concomitant force exerted on the two snap-in tabs 34a1 and directed towards the center of the module 41.

The accurate positioning of the optical guide 30 in the module 41 and its holding in particular in rotation relative to the casing 42, are improved by the presence of two rigid tabs 34a2 arranged at the base 31 of the optical guide 30 while being diametrically opposite and positioned at 90° relative to the snap-in tabs 34a1. Each rigid tab 34a2 protrudes, in the plane of the annular skirt 33 of the optical guide, at a set-back 34a3 made in the annular skirt 33. Two coincident recesses 47a3 are made at the annular edge of the lower cover 42b. As illustrated in FIG. 20, when the optical guide 30 is mounted on the casing 42, the rigid tabs 34a2 are housed in the recesses 47a3.

All the other elements of the optical guide 30 and of the casing 42 are unchanged compared to the third variant of FIGS. 11 to 19.

Tests and Protocols

Tests have been conducted to evaluate the effectiveness of the device of the invention. The efficacy of the device of the invention on the attenuation of the pathology induced by the beta-amyloid injection into mice has been more accurately evaluated. These tests also allowed determining the irradiation protocol that allows acting on the neurodegenerative diseases such as Alzheimer's disease.

The animal model used to test the device of the invention is the non-transgenic model Aβ25-35 of Alzheimer's disease consisting of the intracerebroventricular injection into mice of the Aβ25-35 amyloid peptide in oligomeric form. The presence of amyloid peptide has been identified in the brain of Alzheimer's patients; Aβ25-35 peptide happens to be one of the most neurotoxic ones. It has been shown that the intracerebroventricular injection of the Aβ25-35 peptide results seven days later at the level of the brain in the presence of neuroinflammation and reactive gliosis, the activation of pro-apoptotic caspases, an oxidative stress, a reduction the number of pyramidal cells in the hippocampus, a loss of cholinergic neurons and serious memory problems. In a very interesting manner, the injection of the Aβ25-35 peptide results in the establishment of a pathology which presents all the characteristics of Alzheimer's disease in humans with particularly the accumulation of endogenous AP species but also a hyperphosphorylation of the tau protein, as observed in the physiopathology of Alzheimer's disease.

On day 1, the Aβ25-35 amyloid peptide was injected into a group of mice at a rate of 9 nmol/mouse and the Sc.Aβ peptide (scrambled amyloid-β protein 25-35) into another group of control mice also at a rate of 9 nmol/mouse in order to cause an amyloid toxicity.

Part of the group of mice into which the Aβ25-35 amyloid peptide was injected was subjected to a transcutaneous irradiation treatment from day 1 (2 hours after the injection of the Aβ25-35 amyloid peptide) to day 10. The irradiation treatment was carried out in the head and abdomen. The irradiation devices used are either according to the invention (reference 59 in FIGS. 22 to 26), or outside the scope of the invention (reference 58 in FIGS. 22 to 26). The different devices used and compared will be explained below.

On days 8 to 10, behavioral tests are carried out on all the groups of mice (Sc.Aβ without treatment, Aβ25-35 without treatment, Aβ25-35 with treatment).

The first behavioral test carried out on day 8 evaluates the alteration of the spontaneous spatial memory of the mice by means of a test for evaluating the alternation performance in a Y-maze. The labyrinth therefore includes three arms. Each mouse is positioned at the end of an arm and can move freely in the labyrinth during an 8-minute session. The movement of each mouse including the returns in the same arm are checked visually. An alternation is defined as entries in the three arms on several consecutive occasions. The number of maximum alternations is the total number of entries in the arms minus two. The percentage of alternation is calculated as: (the number of actual alternations/the number of maximum alternations)×100. The results of this first behavioral test are presented in FIGS. 10, 16 and 22.

The second behavioral test carried out on days 9 and 10 evaluates the long-term contextual memory otherwise known as "passive avoidance test". This test is carried out on day 10 in two stages with a training session on day 9. The apparatus under test is a box with two compartments, one of which is lighted and the other is plunged into darkness and equipped with a floor in the form of a grid. A guillotine-type closing door separates the two compartments. Shocks can be generated at the level of the grid floor of the dark compartment. Initially, the door separating the two compartments is closed. For the training session, each mouse is placed in the lighted compartment. After 5 seconds, the door is opened. When the mouse enters the dark compartment, electric shocks are generated on the grid. On day 10, the mouse is again placed in the lighted compartment, the door closed. The door is opened and two parameters are measured: the latency time, that is to say the time after which the mouse enters the dark compartment, and the escape time, that is to say the time after which the mouse leaves the dark compartment. The results of these two subtests (latency time and escape time) are presented in FIGS. 23 and 25.

On day 10, the mice are euthanized. The hippocampus and the frontal cortex of the mice are dissected. The levels of lipid peroxidation in the hippocampus are determined in CHP equivalents per milligrams of tissue and in percentage compared to the control group (Sc.Aβ without treatment). The results are presented in FIG. 24. The level of TNFα (tumor necrosis factor) is also determined in the hippocampus by the enzyme-linked immunosorbent assay ELISA. The results are expressed in percentage relative to the control group (Sc.Aβ without treatment) and presented in FIG. 26.

It should be noted that for the results presented in FIGS. 22 to 26, the results obtained by injection of Sc.Aβ without treatment constitute a first reference control since this injection did not modify the behavior of the mice nor the level of markers tested. The results obtained by injection of Aβ25-35 without treatment constitute a second reference control.

It will also be noted that the indications ### and ## respectively mean a total and excellent adequacy with the control group (Sc.Aβ without treatment), and the indications *** mean a total inadequacy with the control (Sc.Aβ without treatment).

Referring to FIGS. 22 to 26. These figures illustrate the results obtained by the tests mentioned above for irradiation treatments carried out once a day under the following operating conditions:

Reference 56: injection of Sc.Aβ without treatment (control 1)

Reference 57: injection of Aβ25-35 without treatment (control 2)

Reference 58: injection of Aβ25-35 with treatment of 6 minutes once a day simultaneously on the head and on the abdomen by an irradiation device A for which the irradiation modules include a planar transparent lens applied on the skin of mice previously shaved and which includes three light-emitting diodes (LED) which are infrared-emitting at 850 nanometers, three light-emitting diodes (LED) which are red-emitting at 640 nanometers, and a pulsed-type laser diode having a pulse duration comprised between 80 and 100 nanoseconds, a 10 kHz (i.e. 0.1 millisecond) pulse train, preferably between 1 and 20 kHz, typically 15 kHz, emitting at 850 nanometers and having a pulse power of 1 Watt. The treatment is established in pulsed mode at 10 Hertz for the head and for the abdomen.

Reference 59: injection of Aβ25-35 with treatment of 6 minutes once a day simultaneously on the head and on the abdomen by an irradiation device B for which the irradiation modules include an optical guide according to the invention of the fourth variant illustrated in FIGS. 20 and 21, the modules being applied on the head and the abdomen of the unshaven mice. The module includes a light-emitting diode (LED) which is infrared-emitting at 850 nanometers, a light-emitting diode (LED) which is red-emitting at 640 nanometers, and a pulsed-type laser diode having a pulse duration between 80 and 100 nanoseconds, a 10 kHz (i.e. 0.1 millisecond) pulse train, preferably between 1 and 20 kHz, typically 15 kHz, emitting at 850 nanometers and having a pulse power of 1 Watt. The treatment is established in pulsed mode at 10 Hertz for the head and for the abdomen.

It can be observed that the results presented in FIGS. 22 to 26 are very significant for the irradiation device B (reference 59) according to the invention. It is also observed that these results are equivalent to the results obtained for the device A of the prior art. Thus, the optical guide of the invention allows ensuring good treatment efficiency even in the presence of hair on the skin.

For the three variants described above, the optical guide 1, 1a, 30 must be held in position on the head of a user at a very specific area. To do so, the optical guide 1 is mounted on a transcutaneous irradiation module which can be that of FIGS. 11 and 19 for the third variant of the optical guide, an irradiation module including the fourth variant of the optical guide, or any other suitable module that ensures the coaxial holding of the light sources proximally opposite the collecting ends of the diffusion rods. The module also provides means for power supplying the electronic board.

The module must be accurately positioned on the head of the user to irradiate only the concerned area. To do so, a module support described with reference to FIGS. 27 to 35 is provided.

The module support includes one or several ring(s) made of a flexible and/or elastic material making it possible to ensure, by elastic grip, the fixed holding of the transcranial irradiation module. By flexible and/or elastic material is meant a material, for example an elastomer or rubber material that allows the insertion of an essentially cylindrical outer surface module into the ring by spacing of said ring and elastic return against the module. The material could be flexible without being elastic, its spacing for the insertion and the attachment of the module implying a significant extension of the material, the holding of the module in the ring can then be ensured by friction. The support also includes means for a positioning on the area to be irradiated. These means can take the form of a strap, but can also, or additionally, take the form of the support which, by resting on the area to be treated, adapt to this area and are held in place due to this suitable support form.

Reference will be made to FIGS. 27 to 32 to describe the module support of the invention.

The support 61 includes a plurality of rings 62 for holding modules distributed over the surface of the head 63 (for reasons of clarity, all the rings are not referenced in the figures). As a non-limiting example, each ring is made of silicone, has an outer radius of 25 millimeters, an inner radius of 23 millimeters (i.e. a thickness of 2 millimeters), and a height of 6 millimeters. The height must be sufficient for the strength of a module which will be described later. As a variant of the use of silicone, the rings may be made of rubber, of elastomeric material or any other polymeric or non-polymeric material which is flexible enough to allow the insertion and the holding of an essentially cylindrical outer surface module.

The rings 62 are distributed symmetrically on the support, so that when they are positioned on the head 63, the axis of symmetry of the support XX' coincides with the median axis XX' of the head 63 of the user. The rings 62 are connected together by flexible junction elements 64, made for example from the same material as the rings, in this example made of silicone. The junction elements 64 are accurately positioned on the support 61 to allow both the support 61 to adapt to the shape of the head 63 of the user, and to allow the holding of the support on the head 63, as it will be described in detail later.

The rings 62 are distributed as follows: the support 61 provides ten peripheral rings 62a, four second-periphery rings 62b and four central rings 62c. It is understood that this accurate number and this accurate disposition of the rings is given by way of non-limiting example. The number of rings 62 can vary, their position too, while remaining within the scope of the invention.

Referring to FIG. 28 in which the rings 62a, 62b, 62c have been numbered 62a1, 62a2, 62a3, 62a4, 62a5, 62b1, 62b2, 62b3, 62b4, 62c1, 62c2 to describe their functionality, being understood that this FIG. 28 represents only half of the support 61, the four peripheral rings 62a1, 62a2 and the two second-periphery rings 62b1 located towards the front of the head 63 are intended to reach the frontal lobe. The six peripheral rings 62a2, 62a3, 62a4 extending from the second front peripheral ring are intended to reach the temporal lobe. The four central rings 62c1, 62c2 and the four second-periphery rings 62b2, 62b3 located above the patient's ears are intended to reach the parietal lobe. The four rearmost peripheral rings 62a4, 62a5 are intended to reach the cerebellum. And the two second-periphery rings 62b4 located above the rearmost peripheral ring, and the two peripheral rings 62a4 in front of the rearmost peripheral rings 62a5, are intended to reach the occipital lobe. All rings 62 also allow deeper access to the thalamus, the hippocampus and the tonsils.

The four central rings 62c are connected together by central junctions 64a. The second-periphery rings 62b are connected to the central rings 62c by second-periphery junctions 64b. Some second-periphery rings 62b are also connected together by second-periphery junctions 64b. The peripheral rings 62a are each connected to a second-periphery ring 62b by a peripheral junction 64a. On the other hand, the peripheral rings 62a are not connected together by junctions. It is possible to provide that one of the junctions 64a, 64b, 64c includes a flat area allowing to secure a patient's identification label thereto.

The absence of connection between the peripheral rings 62a allows the support 61 to adapt to the shape of the patient's head by opening more or less. Remaining within the scope of the invention, some peripheral rings 62a could be connected together while conferring this adaptation functionality. On the other hand, if all the peripheral rings 62a are connected together, the support 61 will not be able to adapt to different shapes of heads.

Regarding the second-periphery rings 62b, some are connected together so that the support has sufficient strength to remain in place on the head and keep the modules in place in the rings. The fact that some second-periphery rings 62b are not connected together also allows maintaining the functionality of adaptation of the support 61 to any head shape.

The presence or not and the position of the second-periphery junctions 64b and of the peripheral junctions 64a are appreciated by those skilled in the art in a compromise between the rigidity of the support 61 necessary to allow it to be held in position on the head of the patient and to hold the module(s), and the adaptability of the support 61 to any head shape. The presence or not of these junctions can in particular vary according to the number of rings present on the support 61 or even the rigidity of the materials used to make the rings 62 and the junctions 64.

In any event, it is essential that at least part of the peripheral rings 62a are not connected together, and preferably that all the peripheral rings 62a are not connected together. It also appears important for the rigidity of the support that, on the contrary, the central rings 62c are connected together by junctions 64a. The integral connection of the central rings 62c depends on the number of central rings 62c used.

For example, the support 61 can be made in one piece by silicone molding.

Referring to FIG. 33, to further improve the holding of the support 61 on the head and to accurately position the rings 62 towards the areas of the brain to be treated, there is provided a controlled-clamping strap 65. This strap 65 includes a first connecting portion 65a which connects each peripheral ring 62a via a tubular element 66 arranged at the lower peripheral edge of each peripheral ring 62a.

The strap 65 also includes a chin strap 65b connected to the first connecting portion 65a by four connecting elements 65c, passing two by two on either side of the patient's ear. Alternatively, it can be provided that the strap 65 is held in position by Velcro-type bands.

It can be provided that three clamping points 67a, 67b, 67c among which two clamping points 67a, 67b are located at the junction of the connecting elements 65c and of the first connecting portion 65a, and the third clamping point is located at the junction between the chin strap 65b and the two connecting elements 65c.

To further improve the strength of the modules (which will be described later) in the rings 62, it can be provided, with reference to FIG. 32, the presence of a groove 68 at the level of the inner face of the ring 62. This groove 68 is intended to coincide with a circular rib arranged on the outer surface of the associated module. The presence of the groove 68 allows not only improving the strength of the module, but also provides more accurate positioning of the module so that the radiations are accurately directed towards the targeted areas of the brain.

The assembly of the module including the optical guide of the invention, for example the module 41 of the third variant, in a ring 62 is made by coaxial insertion of the module 41 inside the ring 62. The module 41 has to this end a generally cylindrical shape making it possible to ensure its coaxial holding in the ring 62. This coaxial configuration is important because it allows ensuring the positioning and the fixed holding of the module 41 in the axis of the dedicated ring.

As mentioned above, when the rings 62 are provided with an inner groove 68, the outer surface of the module 41 has a corresponding circular rib housed in the groove 68 to ensure the fixed and accurate positioning of the module 41 in the axis of the ring 62.

Thus, the presence of the optical guide 1, 1a, 30 on the irradiation module 41, as well as the holding of the irradiation module(s) 41 by the support 61 allow accurately and effectively irradiating the targeted areas of the brain by increasing the effectiveness of the neurological treatments.

The module support can also take the form of a cap (or even a flexible membrane) intended to be disposed on the head of a patient, cap in which optical guides are plugged, for example. Also, it can be a cap in which orifices are provided to house the optical guides.

The optical guide of the invention also applies to the irradiation of other portions of the body, for example the abdomen independently or concomitantly with an irradiation of the brain.

Alternatively and with reference to FIG. 5a, the diffusion rod 2' consists of two elements: a conduit C in which is housed at least one optical fiber FO which allows conducting the light from a lower end 6' to an opposite end 7'. The optical fiber FO extends longitudinally inside the conduit FO. The conduit C extends longitudinally from the first lower end 6' up to the opposite diffusion end 7' intended to be affixed to the surface to be irradiated. The conduit C has the same shapes as the rod 2 of FIG. 5: lower portion 9' having a diameter D1 and upper portion 10' having a diameter D2, D2<D1. The diffusion rod 2' according to this embodiment can be arranged in the base 3 in the same way as the diffusion rod 2.

Likewise, the shape of the diffusion rod 2a of FIG. 10 can be that of a conduit in which at least one optical fiber can be disposed, the conduit can then be disposed in the base 3a of FIG. 9 in the same way as the diffusion rod 2a.

Also, considering a two-piece diffusion rod, it can be provided a conduit in which a rod 2, 2a is disposed.

The conduit is advantageously made of plastic material and is preferably covered, thereinside, with a reflective material so as to promote the diffusion of light by the optical fiber(s).

In the case where the diffusion rod consists of two elements, it is not necessary to provide a lens or the like at the upper end.

Like the one-piece diffusion rods 2, 2a, the two-piece variant with a conduit can be a component of a transcutaneous irradiation module, in which the optical guide is mounted in an annular casing 4, 4a, 42, the optical fiber(s) being connected to a Laser or infrared light source. Regarding the case with at least one optical fiber, the light source can consist of one or several source(s), for example Laser source(s), which will be connected together by an optical fiber.

Complementarily, in all the variants described above, the lower end of the rod can take several forms: round, triangular, square, etc. In addition, at this end, alternatively or complementarily, a prism can be disposed in front of the lens to improve the diffusion of the light.

The invention claimed is:

1. A transcutaneous irradiation module, comprising an optical guide for diffusing a light radiation through a surface, the optical guide comprising a base, base comprising or being configured to hold at least one diffusion rod whose lower diffusion end protrudes from said base and is configured to be applied on or near said surface, and whose upper collecting end is configured to be located near and opposite a power supplied light source, said diffusion rod comprising a material configured to transmit light from its collecting end up to its diffusion end, the collecting end of said diffusion rod includes a converging lens, and the diffusion end includes a converging lens, the transcutaneous irradiation module further comprising an annular casing including at least one power supplied light source located opposite and near the collecting end of a diffusion rod, the optical guide being mounted in the annular casing and comprises a plurality of light sources, each of the light sources being located opposite and near the collecting end of a diffusion rod wherein the light source comprises at least one infrared laser diode, one red spectrum-emitting light-emitting diode, and one infrared-emitting light-emitting diode, wherein each diffusion rod is associated with a light source.

2. The transcutaneous irradiation module according to claim 1, wherein said diffusion rod is in one piece and is made of a material configured to transmit light from its collecting end up to its diffusion end.

3. The transcutaneous irradiation module according to claim 1, wherein the lower diffusion end is planar.

4. The transcutaneous irradiation module according to claim 1, wherein the diffusion rod is made of polymethyl methacrylate (PMMA), or of glass, or of polycarbonate or of transparent copolyester (PETG) or any other equivalent material with high transparency.

5. The transcutaneous irradiation module according to claim 1, wherein the diffusion rod is in two pieces and consists of a conduit in which at least one optical fiber is disposed.

6. The transcutaneous irradiation module according to claim 5, wherein the conduit is covered, thereinside, with a reflective material.

7. The transcutaneous irradiation module according to claim 1, wherein the base is made of a material configured to transmit light.

8. The transcutaneous irradiation module according to claim 1, wherein the base includes a plurality of through orifices through each of which a removable diffusion rod is housed.

9. The transcutaneous irradiation module according to claim 1, wherein the optical guide is made in one piece integrating the diffusion rod(s).

10. The transcutaneous irradiation module according to claim 1, wherein the diffusion end further includes a prism.

11. The transcutaneous irradiation module according to claim 1, wherein the infrared laser diode is of the pulsed type.

12. The transcutaneous irradiation module according to claim 11, wherein the pulsed-type laser diode emits in the infrared at a wavelength between 700 and 1,200 nanometers, has a pulse duration between 20 and 200 nanoseconds, a pulse train between 1 and 20 kHz and a pulse power between 0.5 and 12 Watts.

13. The transcutaneous irradiation module according to claim 1, wherein the modulation frequency applied to the light-emitting diodes and to the infrared laser is between 1 and 1,000 Hz.

14. A transcutaneous and transcranial irradiation device, further comprising positioning means on the head of a user and at least one ring made of an elastic and/or flexible material and able to ensure the attachment by elastic grip of an irradiation module according to claim 1.

15. The irradiation device according to claim 14, further comprising a plurality of rings connected together by junction elements and in that the rings are symmetrically disposed on either side of an axis coincident with the median axis of the head when the device is in place on the head of the user, in that the rings include peripheral rings at least some of which are not connected together by junction elements.

16. A use of the transcutaneous irradiation module according to claim 1, for diffusing a light radiation through the scalp of a user.

* * * * *